(12) United States Patent
Volkin et al.

(10) Patent No.: US 6,358,744 B1
(45) Date of Patent: Mar. 19, 2002

(54) STABILIZED HUMAN PAPILLOMAVIRUS FORMULATIONS

(75) Inventors: David B. Volkin, Doylestown; Li Shi, Eagleville, both of PA (US); Gautam Sanyal, Marlborough, MA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/624,482

(22) Filed: Jul. 24, 2000

Related U.S. Application Data

(63) Continuation of application No. 09/056,067, filed on Apr. 7, 1998, now abandoned.
(60) Provisional application No. 60/042,808, filed on Apr. 8, 1997, now abandoned.

(51) Int. Cl.[7] .................. G01N 31/00; A61K 39/112
(52) U.S. Cl. ................ 436/8; 436/18; 424/204.1; 424/70.1; 424/70.31; 435/5; 430/493; 530/350; 530/300
(58) Field of Search .............. 424/204.1, 70.1, 424/70.31; 436/8, 300, 18; 435/5; 430/493; 530/350

(56) References Cited

U.S. PATENT DOCUMENTS 6,251,678 B1 * 6/2001 Volkin et al. .................. 436/8

FOREIGN PATENT DOCUMENTS

WO    WO96/29413    9/1996

OTHER PUBLICATIONS

Powell et al. Vaccine Design: The subunit and adjuvant approch, Pharmaceutical Biotechnology, vol. 6, pp. 205, 1995.
Sundaram et al. Journal of Virological Method. vol. 57, pp. 61–70.

* cited by examiner

*Primary Examiner*—Ali R. Salimi
(74) *Attorney, Agent, or Firm*—Joanne M. Giesser; Jack L. Tribble

(57) ABSTRACT

Human papillomavirus (HPV) antigen formulations are disclosed which prevent protein aggregation and show prolonged stability as aqueous solutions. These formulations comprise a salt (such as sodium chloride) and a non-ionic surfactant (Polysorbate 80 such as Tween 80®) in physiologically acceptable concentrations.

15 Claims, 11 Drawing Sheets

SEQUENCE LISTING

<160> NUMBER OF SEQ ID NOS: 35

<210> SEQ ID NO 1
<211> LENGTH: 164
<212> TYPE: DNA
<213> ORGANISM: Synthetic DNA Oligomer

<400> SEQUENCE: 1

```
gaagatctca caaaacaaaa tgtggcggcc tagcgacagc acagtatatg tgcctcctcc      60
taaccctgta tccaaagttg ttgccacgga tgcttatgtt aaacgcacca acatatttta     120
tcatgccagc agttctagac ttcttgcagt gggtcatcct tatt                      164
```

<210> SEQ ID NO 2
<211> LENGTH: 156
<212> TYPE: DNA
<213> ORGANISM: Synthetic DNA Oligomer

<400> SEQUENCE: 2

```
attccataaa aaaggttaac aaaactgttg tgccaaaggt gtcaggatat caatacagag      60
tatttaaggt ggtgttacca gatcctaaca aatttgcatt gcctgactcg tctctttttg     120
atcccacaac acaacgtttg gtatgggcat gcatgt                               156
```

<210> SEQ ID NO 3
<211> LENGTH: 136
<212> TYPE: DNA
<213> ORGANISM: Synthetic DNA Oligomer

<400> SEQUENCE: 3

```
acatgcatgc acaggcctag aggtgggccg gggacagcca ttaggtgtgg gtgtaagtgg      60
acatccttta ctaaataaat atgatgatgt tgaaaattca gggggttacg gtggtaaccc     120
tggacaggat aacagg                                                    136
```

<210> SEQ ID NO 4
<211> LENGTH: 127
<212> TYPE: DNA
<213> ORGANISM: Synthetic DNA Oligomer

<400> SEQUENCE: 4

```
gttaatgtag gtatggatta taaacaaaca caattatgca tggttggatg tgccccccct      60
ttgggcgagc attggggtaa aggtacacag tgtagtaata catctgtaca gaatggtgac     120
```

```
tgcccgc                                                              127

<210> SEQ ID NO 5
<211> LENGTH: 125
<212> TYPE: DNA
<213> ORGANISM: Synthetic DNA Oligomer

<400> SEQUENCE: 5
ccttagaact tattaccagt gttatacagg atggcgatat ggttgacaca ggctttggtg    60
ctatgaattt tgctgatttg cagaccaata atcagatgt tcctcttgac atatgtggca    120
ctgta                                                                125

<210> SEQ ID NO 6
<211> LENGTH: 116
<212> TYPE: DNA
<213> ORGANISM: Synthetic DNA Oligomer

<400> SEQUENCE: 6
tgtaaatatc cagattattt acaaatggct gcagacccat atggtgatag attatttttt    60
tatctacgga aggaacaaat gtttgccaga cattttttta acagggctgg tacccc        116

<210> SEQ ID NO 7
<211> LENGTH: 124
<212> TYPE: DNA
<213> ORGANISM: Synthetic DNA Oligomer

<400> SEQUENCE: 7
ggggtaccgt gggggaacct gtgcctgatg atcttttagt taagggtggt aacaatcgct    60
cgtctgtagc gagtagtata tatgttcaca ccccaagcgg ctctttggtg tcctctgagg    120
caca                                                                 124

<210> SEQ ID NO 8
<211> LENGTH: 113
<212> TYPE: DNA
<213> ORGANISM: Synthetic DNA Oligomer

<400> SEQUENCE: 8
attgtttaat aagccatatt ggctacaaaa agcccaggga cataacaatg gtatttgttg    60
gggtaatcat ctgtttgtta ctgtggtaga taccacacgc agtaccaaca tga           113

<210> SEQ ID NO 9
<211> LENGTH: 113
<212> TYPE: DNA
<213> ORGANISM: Synthetic DNA Oligomer

<400> SEQUENCE: 9
cattatgtgc atccgtatct aaatctgcca catacaccaa ttctgattat aaagagtaca    60
tgcgtcatgt ggaagagttt gatttacaat ttattttca attatgtagc att            113

<210> SEQ ID NO 10
<211> LENGTH: 105
<212> TYPE: DNA
<213> ORGANISM: Synthetic DNA Oligomer

<400> SEQUENCE: 10
acattgtctg ctgaagtaat ggcctatatt cacacaatga atccctctgt tctcgaggac    60
tggaactttg ggttatcgcc tcccccaaat ggtacactcg agcgg                    105
```

<210> SEQ ID NO 11
<211> LENGTH: 155
<212> TYPE: DNA
<213> ORGANISM: Synthetic DNA Oligomer

<400> SEQUENCE: 11

| | | | | | |
|---|---|---|---|---|---|
| ccgctcgagg | atacctatag | gtatgtgcag | tcacaggcca | ttacctgtca | aaagcccact | 60 |
| cctgaaaagg | aaaagcaaga | tccctataag | gacatgagtt | tttgggaggt | taatttaaaa | 120 |
| gaaaagtttt | ctagtgaatt | ggatcagttt | cctttt | | | 155 |

<210> SEQ ID NO 12
<211> LENGTH: 134
<212> TYPE: DNA
<213> ORGANISM: Synthetic DNA Oligomer

<400> SEQUENCE: 12

| | | | | | |
|---|---|---|---|---|---|
| gggacgcaag | ttttttgttac | aaagtggata | taggggacgg | acctctgctc | gtaccggtat | 60 |
| taagcgccct | gctgtttcca | aaccctctac | tgcccctaaa | cgtaagcgca | ccaaaactaa | 120 |
| aaagtaagat | cttc | | | | | 134 |

<210> SEQ ID NO 13
<211> LENGTH: 154
<212> TYPE: DNA
<213> ORGANISM: Synthetic DNA Oligomer

<400> SEQUENCE: 13

| | | | | | |
|---|---|---|---|---|---|
| gaagatctta | cttttttagtt | ttggtgcgct | tacgtttagg | ggcagtagag | ggtttggaaa | 60 |
| cagcagggcg | cttaataccg | gtacgagcag | aggtccgtcc | cctatatcca | ctttgtaaca | 120 |
| aaaacttgcg | tcccaaagga | aactgatcca | attc | | | 154 |

<210> SEQ ID NO 14
<211> LENGTH: 135
<212> TYPE: DNA
<213> ORGANISM: Synthetic DNA Oligomer

<400> SEQUENCE: 14

| | | | | | |
|---|---|---|---|---|---|
| actagaaaac | ttttcttttta | aattaacctc | ccaaaaactc | atgtccttat | agggatcttg | 60 |
| cttttccttt | tcaggagtgg | gcttttgaca | ggtaatggcc | tgtgactgca | catacctata | 120 |
| ggtatcctcg | agcgg | | | | | 135 |

<210> SEQ ID NO 15
<211> LENGTH: 125
<212> TYPE: DNA
<213> ORGANISM: Synthetic DNA Oligomer

<400> SEQUENCE: 15

| | | | | | |
|---|---|---|---|---|---|
| ccgctcgagt | gtaccatttg | ggggaggcga | taacccaaag | ttccagtcct | cgagaacaga | 60 |
| gggattcatt | gtgtgaatat | aggccattac | ttcagcagac | aatgtaatgc | tacataattg | 120 |
| aaaaa | | | | | | 125 |

<210> SEQ ID NO 16
<211> LENGTH: 113
<212> TYPE: DNA
<213> ORGANISM: Synthetic DNA Oligomer

<400> SEQUENCE: 16

| | | | | | |
|---|---|---|---|---|---|
| taaattgtaa | atcaaactct | tccacatgac | gcatgtactc | tttataatca | gaattggtgt | 60 | atgtggcaga tttagatacg gatgcacata atgtcatgtt ggtactgcgt gtg        113

<210> SEQ ID NO 17
<211> LENGTH: 113
<212> TYPE: DNA
<213> ORGANISM: Synthetic DNA Oligomer

<400> SEQUENCE: 17
gtatctacca cagtaacaaa cagatgatta ccccaacaaa taccattgtt atgtccctgg    60 gcttttttgta gccaatatgg cttattaaac aattgtgcct cagaggacac caa         113

<210> SEQ ID NO 18
<211> LENGTH: 104
<212> TYPE: DNA
<213> ORGANISM: Synthetic DNA Oligomer

<400> SEQUENCE: 18
agagccgctt ggggtgtgaa catatatact actcgctaca gacgagcgat tgttaccacc    60
cttaactaaa agatcatcag gcacaggttc ccccacggta cccc                   104

<210> SEQ ID NO 19
<211> LENGTH: 136
<212> TYPE: DNA
<213> ORGANISM: Synthetic DNA Oligomer

<400> SEQUENCE: 19
ggggtaccag ccctgttaaa aaaatgtctg gcaaacattt gttccttccg tagataaaaa    60
aataatctat caccatatgg gtctgcagcc atttgtaaat aatctggata tttacataca   120
gtgccacata tgtcaa                                                  136

<210> SEQ ID NO 20
<211> LENGTH: 125
<212> TYPE: DNA
<213> ORGANISM: Synthetic DNA Oligomer

<400> SEQUENCE: 20
gaggaacatc tgatttattg gtctgcaaat cagcaaaatt catagcacca aagcctgtgt    60
caaccatatc gccatcctgt ataacactgg taataagttc taagggcggg cagtcaccat   120
tctgt                                                              125

<210> SEQ ID NO 21
<211> LENGTH: 127
<212> TYPE: DNA
<213> ORGANISM: Synthetic DNA Oligomer

<400> SEQUENCE: 21
acagatgtat tactcactg tgtacccttta ccccaatgct cgcccaaagg ggggcacat     60 ccaaccatgc ataattgtgt tgtttataa tccataccta cattaaccct gttatcctgt   120
ccagggt                                                            127

<210> SEQ ID NO 22
<211> LENGTH: 116
<212> TYPE: DNA
<213> ORGANISM: Synthetic DNA Oligomer

<400> SEQUENCE: 22
taccaccgta acccctgaa ttttcaacat catcatattt atttagtaaa ggatgtccac    60

-continued ttacacccac acctaatggc tgtccccggc ccacctctag gcctgtgcat gcatgt        116

<210> SEQ ID NO 23
<211> LENGTH: 170
<212> TYPE: DNA
<213> ORGANISM: Synthetic DNA Oligomer

<400> SEQUENCE: 23
acatgcatgc ccataccaaa cgttgtgttg tgggatcaaa agagacgag tcaggcaatg      60 caaatttgtt aggatctggt aacaccacct taaatactct gtattgatat cctgacacct   120
ttggcacaac agttttgtta accttttta tggaataata aggatgaccc              170

<210> SEQ ID NO 24
<211> LENGTH: 150
<212> TYPE: DNA
<213> ORGANISM: Synthetic DNA Oligomer

<400> SEQUENCE: 24
actgcaagaa gtctagaact gctggcatga taaaatatgt tggtgcgttt aacataagca     60
tccgtggcaa caactttgga tacagggtta ggaggaggca catatactgt gctgtcgcta   120
ggccgccaca ttttgttttg tgagatcttc                                   150

<210> SEQ ID NO 25
<211> LENGTH: 27
<212> TYPE: DNA
<213> ORGANISM: Synthetic DNA Oligomer

<400> SEQUENCE: 25
ggaattcaca tgcatgcaca ggcctag                                       27

<210> SEQ ID NO 26
<211> LENGTH: 26
<212> TYPE: DNA
<213> ORGANISM: Synthetic DNA Oligomer

<400> SEQUENCE: 26
ggaattcggg gtaccagccc tgttaa                                        26

<210> SEQ ID NO 27
<211> LENGTH: 45
<212> TYPE: DNA
<213> ORGANISM: Synthetic DNA Oligomer

<400> SEQUENCE: 27
tcgaagactg gaactttggg ttatcgcctc ccccaaatgg tacac                   45

<210> SEQ ID NO 28
<211> LENGTH: 45
<212> TYPE: DNA
<213> ORGANISM: Synthetic DNA Oligomer

<400> SEQUENCE: 28
tcgagtgtac catttggggg aggcgataac ccaaagttcc agtct                   45

<210> SEQ ID NO 29
<211> LENGTH: 45
<212> TYPE: DNA
<213> ORGANISM: Synthetic DNA Oligomer

<400> SEQUENCE: 29
ctcagatctc acaaaacaaa atgtggcggc ctagcgacag cacag                   45

```
<210> SEQ ID NO 30
<211> LENGTH: 35
<212> TYPE: DNA
<213> ORGANISM: Synthetic DNA Oligomer

<400> SEQUENCE: 30
gagagatctt acttttggt tttggtacgt tttcg                           35

<210> SEQ ID NO 31
<211> LENGTH: 34
<212> TYPE: DNA
<213> ORGANISM: Synthetic DNA Oligomer

<400> SEQUENCE: 31
gagagatctt accttttagt tttggcgcgc ttac                           34

<210> SEQ ID NO 32
<211> LENGTH: 31
<212> TYPE: DNA
<213> ORGANISM: Synthetic DNA Oligomer

<400> SEQUENCE: 32
cttaaagctt atgtcacttt ctcttgtatc g                              31

<210> SEQ ID NO 33
<211> LENGTH: 30
<212> TYPE: DNA
<213> ORGANISM: Synthetic DNA Oligomer

<400> SEQUENCE: 33
tgataagctt gctcaatggt tctcttcctc                                30

<210> SEQ ID NO 34
<211> LENGTH: 21
<212> TYPE: DNA
<213> ORGANISM: Synthetic DNA Oligomer

<400> SEQUENCE: 34
tggtcatccc aaatcttgaa a                                         21

<210> SEQ ID NO 35
<211> LENGTH: 21
<212> TYPE: DNA
<213> ORGANISM: Synthetic DNA Oligomer

<400> SEQUENCE: 35
caccgtagtg tttggaagcg a                                         21
```

STABILIZED HUMAN PAPILLOMAVIRUS FORMULATIONS

CROSS-REFERENCE TO RELATED APPLICATIONS

This application is a continuation of application Ser. No. 09/056067, filed Apr. 7, 1998, now abandoned, which claims priority to U.S. provisional application Serial No. 60/042,808, filed Apr. 8, 1997, now abandoned.

STATEMENT REGARDING FEDERALLY SPONSORED RESEARCH

Not applicable.

REFERENCE TO MICROFICHE APPENDIX

Not applicable.

FIELD OF THE INVENTION

The present invention relates to human papillomavirus antigen formulations which show increased antigen stability and reduced antigen aggregation and precipitation. The present invention also relates to methods of preparing adjuvanted HPV vaccines using the human papillomavirus antigen formulations disclosed herein. The present invention also relates to adjuvanted human papillomavirus vaccines generated from these human papillomavirus antigen formulations.

BACKGROUND OF THE INVENTION

Papillomavirus (PV) infections occur in a variety of animals, including humans, sheep, dogs, cats, rabbits, monkeys, snakes and cows. Papillomaviruses infect epithelial cells, generally inducing benign epithelial or fibroepithelial tumors at the site of infection. Papillomaviruses are species specific infective agents.

Papillomaviruses are classified into distinct groups based on the host that they infect. Human papillomaviruses (HPVs) are further classified into more than 70 types based on DNA hybridization studies. PV types appear to be type-specific immunogens in that a neutralizing immunity to infection by one type of papillomavirus does not confer immunity against another type of papillomavirus.

In humans, different HPV types cause distinct diseases. HPV types 1, 2, 3, 4, 7, 10 and 26–29 cause benign warts in both normal and immunocompromised individuals. HPV types 5, 8, 9, 12, 14, 15, 17, 19–25, 36 and 46–50 cause flat lesions in immunocompromised individuals. HPV types 6, 11, 34, 39, 41–44 and 51–55 cause nonmalignant condylomata of the genital or respiratory mucosa. HPV types 16, 18, 31, 33, 35, 45, and 58 cause epithelial dysplasia of the genital mucosa and are associated with the majority of in situ and invasive carcinomas of the cervix, vagina, vulva and anal canal.

Papillomaviruses are small (50–60 nm), nonenveloped, icosahedral DNA viruses that encode for up to eight early and two late genes. The open reading frames (ORFs) of the virus genomes are designated E1 to E8 and L1 and L2, where "E" denotes early and "L" denotes late. L1 and L2 code for virus capsid proteins. The early (E) genes are associated with functions such as viral replication, transcriptional regulation and cellular transformation.

The L1 protein is the major capsid protein and has a molecular weight of 55–60 kDa. L2 protein is a minor capsid protein which has a predicted molecular weight of 55–60 kDa and an apparent molecular weight of 75–100 kDa as determined by polyacrylamide gel electrophoresis. Immunological data suggest that most of the L2 protein is internal to the L1 protein within the viral capsomere. The L1 ORF is highly conserved among different papillomaviruses. The L2 proteins are less conserved among different papillomaviruses.

The L1 and L2 genes have been identified as good targets for immunoprophylaxis. Some of the early genes have also been demonstrated to be potential targets of vaccine development. Studies in the cottontail rabbit papillomavirus (CRPV) and bovine papillomavirus (BPV) systems have shown that immunizations with recombinant L1 and/or L2 proteins (produced in bacteria or by using vaccinia vectors) protected animals from viral infection. Expression of papillomavirus L1 genes in baculovirus expression systems or using vaccinia vectors resulted in the assembly of virus-like particles (VLP) which have been used to induce high-titer virus-neutralizing antibody responses that correlate with protection from viral challenge. Furthermore, the L1 and L2 genes have been used to generate vaccines for the prevention and treatment of papillomavirus infections in animals.

Virus-like particles containing HPV11 L1 protein have been expressed in both insect and mammalian cell systems. Expression of VLPs in yeast cells offers the advantages of being cost-effective and easily adapted to large-scale growth in fermenters. However, the HPV11 L1 protein is expressed at low levels in yeast cells. This was observed to be a result of truncation of the HPV11 L1 mRNA. In contrast, the HPV6 L1 gene is transcribed as full-length mRNA and is expressed to high levels. By modifying the HPV6 L1 DNA to encode the HPV11 L1 protein, it is possible to facilitate the transcription of full-length mRNA resulting in increased HPV11 L1 protein expression.

The L1 and L2 genes have been used to generate vaccines for the prevention and treatment of papillomavirus infections in animals. HPV type 16 L1 and L2 genes have been cloned into a vaccinia virus vector and infected CV-1 mammalian cells with the recombinant vector to produce virus-like particles (VLP).

Bacterially-derived recombinant bovine papillomavirus L1 and L2 have been generated. Neutralizing sera to the recombinant bacterial proteins cross-reacted with native virus at low levels, presumably due to differences in the conformations of the native and bacterially-derived proteins.

Recombinant baculoviruses expressing HPV16 L1 or HPV16 L2 ORFs have been used to infect insect SF9 cells and produce L1 and L2 proteins. Western blot analyses showed that the baculovirus-derived L1 and L2 proteins reacted with antibody to HPV16. The baculovirus derived L1 forms VLPs.

Jansen et al. (1995, *Vaccine* 13(16):1509–1514) use a running buffer comprising sodium chloride and Tween 80® during purification of L1 and L1+L2 VLPs from cottontail rabbit papillomavirus.

At present, purified recombinant HPV VLP formulations must be stored at high NaCl concentrations to prevent aggregation in solution. At low ionic strengths, HPV VLPs aggregate to the point of being precipitated out of solution. Based on these and other related observations, HPV bulk solutions have been stored frozen in the presence of high concentrations of NaCl (1.25–2.5 M). Highly aggregated samples of HPV 11 VLP manifest poor in vitro antigenicity as measured by RIA, EIA or BIA core assays. Therefore, a need exists to prepare an aqueous HPV VLP formulation which is stable at physiological salt conditions as well as

SUMMARY OF THE INVENTION

The present invention relates to human papillomavirus (HPV) antigen formulations which prevent antigen aggregation and increase antigen stability at physiological salt concentrations in the presence of a surfactant.

The present invention also relates to the generation of an adjuvanted HPV vaccine which is formed by mixing an HPV antigen formulation of the present invention with a biologically effective amount of an adjuvant to form an adjuvanted HPV vaccine.

The HPV antigen formulations and adjuvanted vaccines of the present invention include but are not solely limited to, as the antigen component, virus-like particles generated as a recombinant HPV subunit vaccine comprising either L1 or a combination of L1 and L2 proteins, from HPV types 6a, 6b, 11, 16 and 18. It is within the scope of this invention to stabilize monovalent forms of this recombinant vaccine as well as divalent forms (such as but in no way limited to recombinant HPV 11 L1, HPV 16 L1 and HPV 6a L1), and multivalent forms (such as but in no way limited to recombinant HPV 11 L1, HPV 6a L1, HPV 16 L1 and HPV 18 L1).

The present invention also relates to HPV antigen formulations which comprise a physiological salt concentration and a surfactant to provide increased stabilization of the vaccine component of the formulation at temperatures above 0° C. The HPV formulations of the present invention should be amenable to prolonged storage for periods up to at least one month to about two years at about 2° C. to about 8° C.

An embodiment of the present invention relates to HPV antigen formulations wherein the formulation comprises a physiologically acceptable salt, including but not necessarily limited to sodium chloride, sodium sulfate, and ammonium sulfate. The purpose of inclusion of a salt in the formulation is to attain the desired ionic strength. Contributions to ionic strength may come from ions produced by the buffering compound, including but not limited to phoshate, citrate, acetate, succinate, Tris-HCl, MOPS, etc., as well as from the ions of non-buffering salts.

Another embodiment of the present invention relates to HPV antigen formulations wherein the formulation comprises a non-ionic surfactant, including but not necessarily limited to polyoxyethylene sorbitan fatty acid esters (Polysorbates) such as Polysorbate 80 (e.g., Tween 80®), Polysorbate 60 (e.g., Tween 60®) and Polysorbate 20 (e.g., Tween 20®), polyoxyethylene alkyl ethers (e.g., Brij 58®, Brij 35®), as well as others including but not limited to Triton X-100®, Triton X-114®, NP40®, Span 85 and the Pluronic series of non-ionic surfactants (e.g., Pluronic 121).

An additional emobodiment of the present invention relates to an HPV antigen formulation wherein the formulation comprises a non-ionic surfactant as disclosed above and present in a range up to about 0.2% w/v, the physiologically acceptable salt being sodium chloride at a concentration from about 10 mM to about 500 M, in the presence of a physiologically acceptable buffer.

Another emobodiment of the present invention relates to an HPV antigen formulation wherein the formulation comprises a non-ionic surfactant as disclosed above and present in a range up to about 0.2% w/v, the physiologically acceptable salt being sodium chloride at a concentration from about 50 mM to about 400 mM, in the presence of a physiologically acceptable buffer.

Yet another emobodiment of the present invention relates to an HPV antigen formulation wherein the formulation comprises a non-ionic surfactant as disclosed above and present in a range up to about 0.2% w/v, the physiologically acceptable salt being sodium chloride at a concentration from about 150 mM to about 300 mM, in the presence of a physiologically acceptable buffer.

Another embodiment of the present invention relates to a HPV antigen formulation wherein the physiologically acceptable salt is sodium chloride at a concentration from about 10 mM to about 500 mM, and the non-ionic surfactant, Polysorbate 80 (including but not limited to Tween 80®), is present in a range up to about 0.2% w/v, in the presence of a physiologically acceptable buffer.

A specific embodiment of the present invention relates to a HPV antigen formulation wherein the physiologically acceptable salt is sodium chloride at a concentration from about 10 mM to about 500 mM, and the non-ionic surfactant, Polysorbate 80 (including but not limited to Tween 80®), is present in a range from about 0.01% to about 0.1% w/v, in the presence of a physiologically acceptable buffer.

A preferred embodiment of the present invention relates to a HPV antigen formulation wherein sodium chloride is present in concentration from about 50 mM to about 400 mM, Polysorbate 80 (including but not limited to Tween 80®), is present in a percentage range in amounts from about 0.01% to about 0.1% w/v, in the presence of a physiologically acceptable buffer.

An especially preferred embodiment of the present invention relates to a HPV antigen formulation wherein sodium chloride is present in concentration from about 150 mM to about 300 mM, Polysorbate 80 (including but not limited to Tween 80®), is present in a percentage range in amounts from about 0.01% to about 0.1% w/v, in the presence of a physiologically acceptable buffer.

It will be known to one of skill in the art to provide the HPV antigen formulations of the present invention in a physiologically acceptable buffer, preferably but not necessarily limited to a formulation buffered by phosphate, citrate, acetate, succinate, Tris-HCl, or MOPS, preferably but not limited to a pH range from about pH 5.0 to 9.0, and especially within a pH range of about pH 6.0 to about 8.0.

The present invention also relates to methods of generating HPV vaccine formulations which involve using the HPV antigen formulation of the present invention. These improved methods of generating either an alum- or non-alum based HPV vaccine are described herein.

The present invention also relates to adjuvanted HPV vaccines wherein an biologically effective amount of an adjuvant is combined with a biologically effective amount of an antigen-containing formulation as disclosed herein.

The term "PV" as used herein is the abbreviation for "papillomavirus."

The term "HPV" as used herein is the abbreviation for "human papillomavirus."

The term "VLP" as used herein is the abbreviation for "viral-like particle."

The term "physiologically acceptable" as used herein means a buffer, an excipient or a salt wherein either the concentration or ionic strength is such that the formulation is biologically compatible with the immunized target host, such as a human.

DETAILED DESCRIPTION OF THE INVENTION

Figure 1:
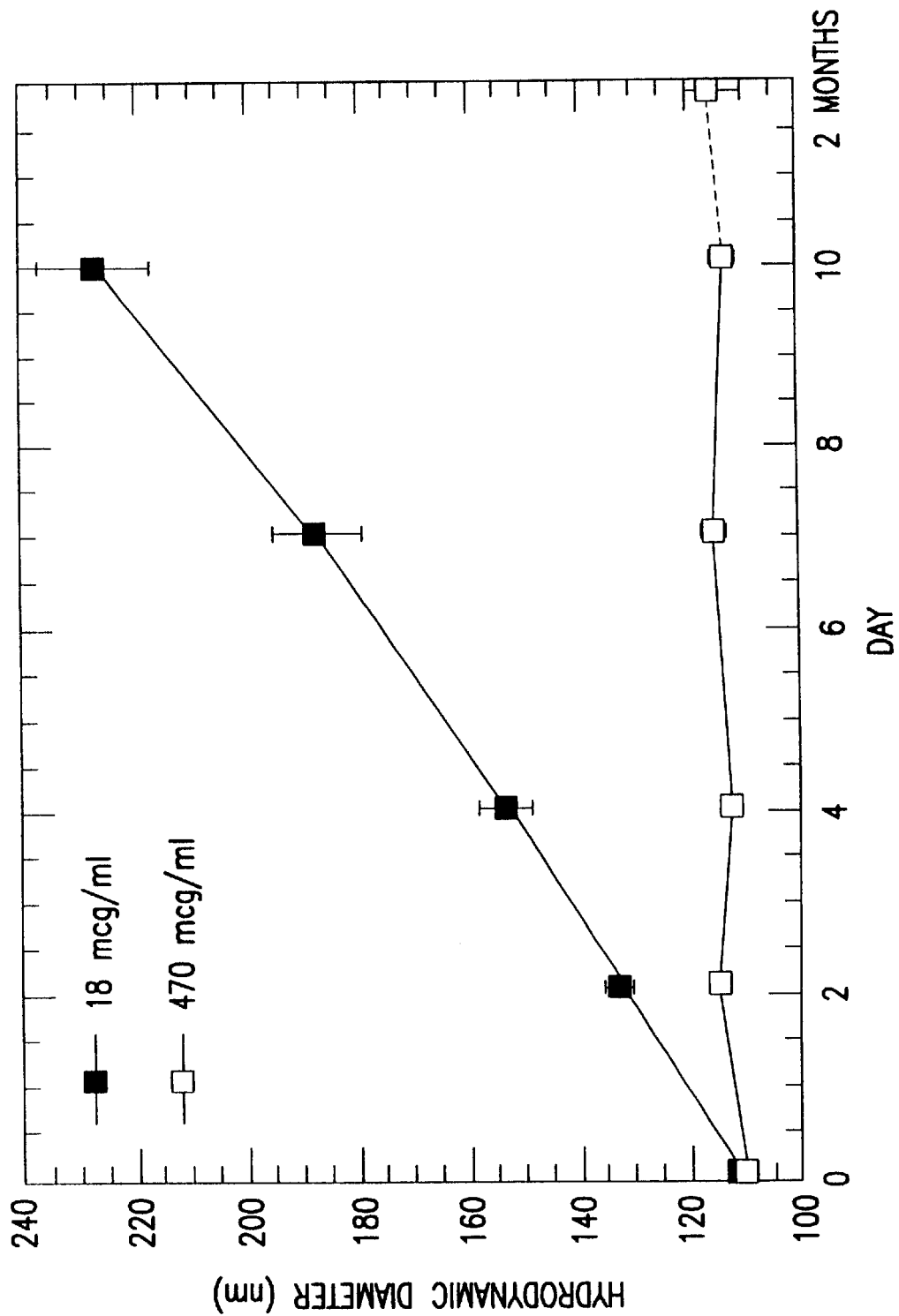
FIG. 1 shows the effect of protein dilution on hydrodynamic size over time for HPV 11 L1 VLP (50 mM MOPS, pH 7.0, 1.25 M NaCl) over a period of 2 months at 4° C. (□) 470 mcg/mL; (■) 18 mcg/mL.

The present invention relates to human papillomavirus (HPV) antigen formulations which prevent antigen aggregation and increase antigen stability at physiological salt concentrations in the presence of a surfactant.

The present invention also relates to the generation of an adjuvanted HPV vaccine which is formed by mixing an HPV antigen formulation of the present invention with a biologically effective amount of an adjuvant to form an adjuvanted HPV vaccine.

The HPV antigen formulations and adjuvanted vaccines of the present invention include but are not solely limited to, as the antigen component, virus-like particles generated as a recombinant HPV subunit vaccine comprising either L1 or a combination of L1 and L2 proteins, from HPV types 6a, 6b, 11, 16 and 18. It is within the scope of this invention to stabilize monovalent forms of this recombinant vaccine as well as divalent forms (such as but in no way limited to recombinant HPV 11 L1, HPV 16 L1 and HPV 6a L1), and multivalent forms (such as but in no way limited to recombinant HPV 11 L1, HPV 6a L1, HPV 16 L1 and HPV 18 L1). To this end, while recombinant HPV 11 L1 VLPs is used in the exemplification of the invention, this in no way limits the HPV types which may be generated for stabilization in the antigen formulations of this invention. In fact, it is apparent upon review of this disclosure that the vaccine formulations disclosed herein may be used to stabilize other vaccine formulations, including but not solely limited to other HPV-based VLPs. For example, the HPV vaccine formulations of the present invention include but are not solely limited to virus-like particles generated as a recombinant HPV subunit vaccine comprising either L1 or a combination of L1 and L2 proteins, from HPV types 6a, 6b, 11, 16 and 18. Therefore, as noted above, it is also apparent that the formulations of the present invention will be useful to stabilize various divalent and multivalent formulations, including but not limited to divalent (such as recombinant HPV 11 L1 and HPV 6a L1) and multivalent (such as recombinant HPV 11 L1, HPV 6a L1, HPV 16 L1 and HPV 18 L1) HPV formulations.

Therefore, the present invention relates to antigen formulations comprising a non-ionic surfactant which stabilize HPV VLPs at physiologically active salt and buffer conditions throughout a range of useful protein concentrations and preferred storage temperatures. The HPV formulations of the present invention should be amenable to prolonged storage for periods up to at least one month to about two years at about 2° C. to about 8° C. These formulations may be mixed with an adjuvant, including known alum-containing adjuvants such as aluminum phosphate, aluminum hydroxyphosphate and aluminum oxyhydroxide. It will also be useful to use the antigen formulations of the present invention with non-alum adjuvants, especially non-alum adjuvants which are negatively effected by high ionic strength formulations known to be utilized for HPV VLPs.

At low ionic strength, HPV 11 L1 VLP is known to aggregate to the point of being precipitated out of solution. Highly aggregated samples of HPV 11 L1 VLP are known to manifest poor in vitro antigenicity (such as RIA, EIA or BIA core assays). Data in Example Section 3 show that an HPV 11 VLP L1 (470 mcg/mL in 50 mM MOPS/1.25 M NaCl) was thawed and a portion of the solution was diluted to 18 mcg/mL in the same buffer. The lower protein concentration solution aggregated over time even though the NaCl concentration was maintained at 1.25 M NaCl.

Therefore, high salt concentrations alone do not prevent HPV VLP aggregation. Data is presented in Example Section 4 testing various NaCl concentration ranges (via either storage or dialysis of bulk solution over a short time period) show that a decrease in NaCl concentration to a low level (about 150 mM NaCl and below) results in protein aggregation (followed by precipitation). To circumvent this problem, solutions containing HPV 11 L1 VLP can be stored frozen in the presence of high concentrations of NaCl (from about 1.25M–2.5M). A portion of the invention as disclosed herein relates to various formulations comprising HPV VLPs that resist aggregation at physiologic salt concentrations within useful temperature ranges. The formulations of the present invention facilitate long term storage of stable HPV VLPs solutions at 4° C. and allow for useful immunogenicity studies of HPV alone or in the presence of either aluminum salt adjuvants or non-aluminum adjuvants.

In addition, it is disclosed in Example Section 5 that contacting HPV VLPs with various surfaces will also affect aggregation. It is shown herein that increasing the surface area for contact with an HPV VLP (e.g., dialysis membrane or storage tube) increases the hydrodynamic size of the VLP. This increase in aggregation leads to a concomitant decrease in protein concentration of the HPV VLP solution, indicating adsorption of HPV VLPs on the membrane surface and suggesting a correlation between surface adsorption and aggregation. Therefore, it is also within the scope of the invention to contact the vaccine to a preferred container surface. The data indicates that HPV 11 L1 VLPs (50 mM MOPS/1.25 M NaCl, pH 7.0) incubated at room temperature for 24 hours show significant adsorption to borosilicate glass while no significant adsorption is seen in polystyerene.

Example Section 6 contains data indicating preferred excipients and salts for inclusion in the formulations of the present invention.

Therefore, the essence of the present invention relates to HPV antigen formulations which comprise physiologic salt concentrations wherein a non-ionic surfactant has been added such that the antigen component of the formulation possesses prolonged stability at temperatures from about 0° C. to about 40° C. as well as resisting aggregation often seen with known HPV formulations. To this end, the present invention relates to HPV vaccine formulations which comprise a salt, including but not necessarily limited to sodium chloride, sodium sulfate, and ammonium sulfate, present at an ionic strength which is physiologically acceptable to the host. The purpose of inclusion of a salt in the formulation is to attain the desired ionic strength. Contributions to ionic strength may come from ions produced by the buffering compound as well as from the ions of non-buffering salts.

An especially preferred aspect of the present invention relates to HPV antigen formulations which comprise a salt at a physiologically acceptable level wherein a minimal amount of a non-ionic surfactant is added to provide increased stabilization of the vaccine component of the formulation. Non-ionic surfactants which for use in the antigen formulations of the present invention include but are not limited to polyoxyethylene sorbitan fatty acid esters, including but not limited to Polysorbate 80 (Tween 80®), Polysorbate 60 (Tween 60®) and Polysorbate 20 (Tween 20®), polyoxyethylene alkyl ethers, including but not limited to Brij 58®, Brij 35®, as well as others such as Triton X-100®, Triton X-114®, NP40®, Span 85 and the Pluronic series of non-ionic surfactants (e.g., Pluronic 121).

An additional emobodiment of the present invention relates to an HPV antigen formulation wherein the formulation comprises a non-ionic surfactant as disclosed above and present in a range up to about 0.2% w/v, the physiologically acceptable salt being sodium chloride at a concentration from about 10 mM to about 500 mM, in the presence of a physiologically acceptable buffer.

Another emobodiment of the present invention relates to an HPV antigen formulation wherein the formulation comprises a non-ionic surfactant as disclosed above and present in a range up to about 0.2% w/v, the physiologically acceptable salt being sodium chloride at a concentration from about 50 mM to about 400 mM, in the presence of a physiologically acceptable buffer.

Yet another emobodiment of the present invention relates to an HPV antigen formulation wherein the formulation comprises a non-ionic surfactant as disclosed above and present in a range up to about 0.2% w/v, the physiologically acceptable salt being sodium chloride at a concentration from about 150 mM to about 300 mM, in the presence of a physiologically acceptable buffer.

Another embodiment of the present invention relates to a HPV antigen formulation wherein the physiologically acceptable salt is sodium chloride at a concentration from about 10 mM to about 500 mM, and the non-ionic surfactant, Polysorbate 80 (including but not limited to Tween 80®), is present in a range up to about 0.2% w/v, in the presence of a physiologically acceptable buffer.

A specific embodiment of the present invention relates to a HPV antigen formulation wherein the physiologically acceptable salt is sodium chloride at a concentration from about 10 mM to about 500 mM, and the non-ionic surfactant, Polysorbate 80 (including but not limited to Tween 80®), is present in a range from about 0.01% to about 0.1% w/v, in the presence of a physiologically acceptable buffer.

A preferred embodiment of the present invention relates to a HPV antigen formulation wherein sodium chloride is present in concentration from about 50 mM to about 400 mM, Polysorbate 80 (including but not limited to Tween 80®), is present in a percentage range in amounts from about 0.01% to about 0.1% w/v, in the presence of a physiologically acceptable buffer.

An especially preferred embodiment of the present invention relates to a HPV antigen formulation wherein sodium chloride is present in concentration from about 150 mM to about 300 mM, Polysorbate 80 (including but not limited to Tween 80®), is present in a percentage range in amounts from about 0.01% to about 0.1% w/v, in the presence of a physiologically acceptable buffer.

It will be known to one of skill in the art to provide the HPV antigen formulations of the present invention in a physiologically acceptable buffer, preferably but not necessarily limited to a formulation buffered by phosphate, citrate, succinate, acetate, Tris-HCl, or MOPS, within a pH range including but not limited to about 5.0 to about 9.0, preferably a pH range from about 6.0 to about 8.0.

The formulation described in the present invention allows storage of HPV solutions at near physiologic salt concentrations in the unfrozen state. Therefore, it will result in elimination of freezing and thawing steps and will allow direct formulation of HPV VLP solutions with adjuvants, either by adsorption of HPV to aluminum adjuvant or preparation with non-aluminum adjuvants, at the appropriate physiologic ionic strength condition.

Therefore, the present invention discloses improved methods of preparing adjuvanted HPV vaccines which does not require such severe gradients in temperature and salt concentration prior to mixing with an alum-containing adjuvant. For example, the antigen formulation of the present invention may be prepared and stored at 4° C. prior to mixing with an aluminum adjuvant. This pre-alum antigen formulation is mixed with an aluminum adjuvant such as aluminum phosphate, aluminum hydroxyphosphate and aluminum oxyhydroxide. A preservative such as thimersol may be added if desired. The method of the present invention should allow for prolonged storage of the original antigen formulation at temperatures ranging from about 2° C. to about 8° C. for a period of up to at least two years.

It is evident upon review of this disclosure that one advantage of the HPV antigen formulations of the present invention is their ability to be combined directly with either an alum or non-alum adjuvant at physiologically acceptable concentrations. It is also evident upon review of this disclosure that another advantage is the increased stability at temperatures above freezing, from about 0° C. to about 40° C., and especially from between about 2° C. and 8° C. such that these formulations may be added directly to an appropriate alum- or non-alum containing adjuvant. In other words, the formulations described herein are also amenable for direct formulation of HPV solutions with non-alum adjuvants at physiologic salt concentrations.

While the above-mentioned exemplified formulations are preferred, it is evident from the teachings of this specification that various additional formulations are contemplated. It is taught herein that the exemplified as well as the additional antigen formulations of the present invention will comprise a salt at a physiologically acceptable ionic strength to the host, a physiologically acceptable buffer and a surfactant at a biologically acceptable concentration such that the vaccine component will enjoy increased stability, reduction in a tendency to aggregate or precipitate from solution, as well as being amenable to storage at more convenient temperatures for prolonged periods of time.

The dosage regimen utilizing the HPV vaccine formulations of the present invention may be selected in accordance with a variety of factors including type, species, age, weight, sex and medical condition of the patient; the severity of the condition to be treated; the route of administration; the renal and hepatic function of the patient; and the particular compound thereof employed. A physician of ordinary skill can readily determine and prescribe the effective amount of the HPV vaccine required to prevent, counter or arrest the progress of the condition.

The following examples are provided as illustrative of the present invention without, however, limiting the same thereto.

EXAMPLE 1

OVEREXPRESSION OF RECOMBINANT HPV 11 L1 VLP

Construction of the Synthetic L1 Gene

The overexpression and purification of the HPV11 L1 VLP is described in U.S. application Ser. Nos. 08/413,571 and 08/413,572, both filed Mar. 30, 1995, and is also presented in this Example section solely to exemplify, but by no means to limit the methods which may be used in generating recombinant HPV VLPs. This specification discloses the use of recombinant HPV11 L1 and HPV16 L1 to exemplify the formulations of the present invention. It will be known to one of ordinary skill in the art that known recombinant DNA methodology may be used to generate recombinant HPV VLPs recited in the present specification. It will also be known that hosts other than yeast may be used to overexpress HPV VLPs which will be utilized in the antigen formulations of the present invention.

The 1.5 kbp open reading frame of HPV11 L1 was constructed using synthetic DNA oligomers ordered from Midland Reagent Company. These oligomers were supplied containing 5' terminal phosphates. A total of 24 oligomers were required and are listed below:

241-1
5'-GAAGATCTCACAAAACAAAATGTGGCGGCCTAG
CGACAGCACAGTATATGTGCCTCCTCCTAACCCTGT
ATCCAAAGTTGTTGCCACGGATGCTTATGT
TAAACGCACCAACATATTTTATCATGCCAGCAG
TTCTAGACTTCTTGCAGTGGGTCATCCTTATT-3'
(SEQ ID NO:1)
2412
5'-ATTCCATAAAAAAGGTTAACAAAACTGTTGTGCC
AAAGGTGTCAGGATATCAATACAGAGTATTTAAGGT
GGTGTTACCAGATCCTAACAAATTTGCATTGCC
TGACTCGTCTCTTTTTGATCCCACAACAC
AACGTTTGGTATGGGCATGCATGT-3' (SEQ ID NO:2)
241-3
5'-ACATGCATGCACAGGCCTAGAGGTGGGCCGGGG
ACAGCCATT AGGTGTGGGTGTAAGTGGACATCCT
TTACTAAATAAATATGATGATGTTGAAAATTC
AGGGGGTTACGGTGGTAACCCTGGACAGGAT
AACAGG-3' (SEQ ID NO:3)
241-4
5'-GTTAATGTAGGTATGGATTATAAACAAACACAAT
TATGCATGGTTGGATGTGCCCCCCCTTTGGGCGAG
CATTGGGGTAAAGGTACACAGTGTAGTAATACATCT
GTACAGAATGGTGACTGCCCGC-3' (SEQ ID NO:4)
241-5
5'-CCTTAGAACTTATTACCAGTGTTATACAGGATGGC
GATATGGTTGACACAGGCTTTGGTGCTATGAATTT
TGCTGATTTGCAGACCAATAAATCAGATGTTCCTC
TTGACATATGTGGCACTGTA-3' (SEQ ID NO:5)
241-6
5'-TGTAAATATCCAGATTATTTACAAATGGCTGCAGA
CCCATATGGTGATAGATTATTTTTTATCTACGGA
AGGAACAAATGTTTGCCAGACATTTTTTAAC
AGGGCTGGTACCCC-3' (SEQ ID NO:6)
241-7
5'-GGGGTACCGTGGGGGAACCTGTGCCTGATGATC
TTTTAGTTAAGGGTGGTAACAATCGCTCGTCTGTA
GCGAGTAGTATATATGTTCACACCCCAAGCGGCT
CTTTGGTGTCCTCTGAGGCACA-3' (SEQ ID NO:7)
241-8
5'-ATTGTTTAATAAGCCATATTGGCTACAAAAGCCC
AGGGACATAACAATGGTATTTGTTGGGGTAATCA
TCTGTTTGTTACTGTGGTAGATACCACACGCA
GTACCAACATGA-3' (SEQ ID NO:8)
241-9
5'-CATTATGTGCATCCGTATCTAAATCTGCCACATACA
CCAATTCTGATTATAAAGAGTACATGCGTCATGT
GGAAGAGTTTGATTTACAATTTATTTTTCAATTATGT
AGCATT-3' (SEQ ID NO:9)
241-10
5'-ACATTGTCTGCTGAAGTAATGGCCTATATTCACAC
AATGAATCCCTCTGTTCTCGAGGACTGGAACTTTG
GGTTATCGCCTCCCCCAAATGGTACACTCGAGCGG-
3' (SEQ ID NO:10)
241-11
5'-CCGCTCGAGGATACCTATAGGTATGTGCAGTCACA
GGCCATTACCTGTCAAAAGCCCACTCCTGAAAAG
GAAAAGCAAGATCCCTATAAGGACATGAGTTTTTG
GGAGGTTAATTTAAAAGAAAAGTTTTC
TAGTGAATTGGATCAGTTTCCTTT-3' (SEQ ID NO:11)
241-12
5'-GGGACGCAAGTTTTTGTTACAAAGTGGATATAGG
GGACGGACCTCTGCTCGTACCGGTATTAAGCGCCC

TGCTGTTTCCAAACCCTCTACTGCCCCTAAACGTAA
GCGCACCAAAACTAAAAAGTAAGATCT TC-3' (SEQ
ID NO:12)
241-13
5'-GAAGATCTTACTTTTTAGTTTTGGTGCGCTTACGT
TTAGGGGCAGTAGAGGGTTTGGAAACAGCAGGGC
GCTTAATACCGGTACGAGCAGAGGTCCGTCCCCT
ATATCCACTTTGTAACAAAAACTTGCGTC
CCAAAGGAAACTGATCCAATTC-3' (SEQ ID NO:13)
241-14
5'-ACTAGAAAACTTTTCTTTTAAATTAACCTCCCAAA
AACTCATGTCCTTATAGGGATCTTGCTTTTCCTT
TTCAGGAGTGGGCTTTTGACAGGTAATGGCCTGT
GACTGCACATACCTATAGGTATCCTCGAGCGG-3'
(SEQ ID NO:14)
241-15
5'-CCGCTCGAGTGTACCATTTGGGGGAGGCGATAAC
CCAAAGTTCCAGTCCTCGAGAACAGAGGGATTCA
TTGTGTGAATATAGGCCATTACTTCAGCAGACAATG
TAATGCTACATAATTGAAAAA-3' (SEQ ID NO:15)
241-16
5'-TAAATTGTAAATCAAACTCTTCCACATGACGCATG
TACTCTTTATAATCAGAATTGGTGTATGTGGCAGAT
TTAGATACGGATGCACATAATGTCATGTTGGTACTG
CGTGTG-3' (SEQ ID NO:16)
241-17
5'-GTATCTACCACAGTAACAAACAGATGATTACCCCA
ACAAATACCATTGTTATGTCCCTGGGCTTTTTGTAG
CCAATATGGCTTATTAAACAATTGTGCCTCAGAGGA
CACCAA-3' (SEQ ID NO:17)
241-18
5'-AGAGCCGCTTGGGGTGTGAACATATATACTACTC
GCTACAGACGAGCGATTGTTACCACCCTTAACTAA
AAGATCATCAGGCACAGGTTCCCCCACGG
TACCCC-3' (SEQ ID NO:18)
241-19
5'-GGGGTACCAGCCCTGTTAAAAAAATGTCTGGCA
AACATTTGTTCCTTCCGTAGATAAAAAAATAATCTA
TCACCATATGGGTCTGCAGCCATTTGTAAATAATC
TGGATATTTACATACAGTGCCACATATGTCAA-3'
(SEQ ID NO:19)
241-20
5'-GAGGAACATCTGATTTATTGGTCTGCAAATCAGC
AAAATTCATAGCACCAAAGCCTGTGTCAACCATATC
GCCATCCTGTATAACACTGGTAATAAGTTCTAAG
GGCGGGCAGTCACCATTCTGT-3' (SEQ ID NO:20)
241-21
5'-ACAGATGTATTACTACACTGTGTACCTTTACCCCA
ATGCTCGCCCAAAGGGGGGGCACATCCAACCATG
CATAATTGTGTTTGTTTATAATCCATACCTACATTAA
CCCTGTTATCCTGTCCAGGGT-3' (SEQ ID NO:21)
241-22
5'-TACCACCGTAACCCCCTGAATTTTCAACATCATC
ATATTTATTTAGTAAAGGATGTCCACTTACACCCAC
ACCTAATGGCTGTCCCCGGCCCACCTCTAGGCCT
GTGCATGCATGT-3' (SEQ ID NO:22)
241-23
5'-ACATGCATGCCCATACCAAACGTTGTGTTGTGGG
ATCAAAAAGAGACGAGTCAGGCAATGCAAATTTG
TTAGGATCTGGTAACACCACCTTAAATACTCTGTAT
TGATATCCTGACACCTTTGGCACAACAGTTTTGT
TAACCTTTTTTATGGAATAATAAGGATGACCC-3'
(SEQ ID NO:23)
241-24
5'-ACTGCAAGAAGTCTAGAACTGCTGGCATGATAAA
ATATGTTGGTGCGTTTAACATAAGCATCCGTGGCA
ACAACTTTGGATACAGGGTTAGGAGGAGGCACAT
ATACTGTGCTGTCGCTAGGCCGCCACATTTTGTTTT
GTGAGATCTTC-3' (SEQ ID NO:24)

Oligomers forming complementary pairs (#241-1 and #241-24, #241-2 and #241-23, #241-3 and #241-22, #241-4 and #241-21, #241-5 and #241-20, #241-6 and #241-19, #241-7 and #241-18, #241-8 and #241-17, #241-9 and #241-16, #241-10 and #241-15, #241-11 and #241-14, #241-12 and #241-13) were annealed in separate tubes containing 2.5 mM Tris, pH 7.5, 0.25 mM EDTA. Tubes were heated to 98° C. for 4 min and then placed in 200 ml of 98° C. water in a 250 ml beaker to cool slowly. When the water cooled to room temperature, the annealed pairs were added to tubes as designated: fragment A (oligomer pairs #241-1 & 24, and -2 & 23); fragment B (#241-3 & 22, -4 & 21, -5 & 20, and -6 &19); fragment C (#241-7 &18, -8 &17, -9 &16 and -10 &15) and fragment D (#241-11 &14 and -12 &13). These oligomer pair mixes were heated to 62° C. for 2 min and then cooled slowly as before. The contents of each tube were ligated overnight at 23° C. using T4 DNA ligase (Boehringer Mannheim, Inc.) and the reagents supplied by the manufacturer.

After ligation, fragment B required PCR amplification to increase the amount of full-length product. This required ten cycles of 940C, 1 min; 48° C., 1 min; 72° C., 1 min followed by 10 min at 72° C. in an Applied Biosystems thermocycler using Boehringer Mannheim Taq polymerase and the oligomer primers:
5'-GGAATTCACATGCATGCACAGGCCTAG-3' (SEQ ID NO:25) and
5'-GGAATTCGGGGTACCAGCCCTGTTAA-3' (SEQ ID NO:26).

The ligated products and the fragment B PCR product were digested with restriction enzymes (Boehringer Mannheim, Inc.) as follows: fragment A was digested with Bgl II and Sph I; fragment B, Sph I and Kpn I; fragment C, Kpn I and Xho I; and fragment D, Xho I and Bgl II. The digested fragments were separated on low melting point agarose (FMC BioProducts) gels and correctly sized fragments isolated by excision of the band and digestion of the agarose using Agarase™ (Boehringer Mannheim, Inc.) as recommended by the supplier. The fragments A, B and D were recovered by ethanol precipitation and then separately ligated into the vector pSP72 (Promega, Inc.) that had been similarly digested with restriction enzymes to match each fragment being ligated.

The Kpn I Xho I digested fragment C was first ligated to the annealed oligomers
5'-TCGAAGACTGGAACTTTGGGTTATCGCCTCCCCC AAATGGTAC AC-3'; (SEQ ID NO:27) and
5'-TCGAGTGTACCATTTGGGGGAGGCGATAACCCAA AGTTCCAGT CT-3' (SEQ ID NO:28).

Fragment C was then recleaved with Xho I and the 450 bp KpnI XhoI fragment was ligated with the Kpn I, Xho I-digested pSP72 vector. The ligation mixes were used to transform *Escherichia coli* strain DH5 competent cells (Gibco BRL, Gaithersburg, Md.). Transformants were screened for insert-containing clones by colony hybridization (J. Sambrook et al., Molecular Cloning: A Laboratory Manual, 2nd edition, Cold Spring Harbor Laboratory Press, 1989). Plasmid DNA was isolated from the positive clones using a Wizard miniprep kit (Promega Corp.) and then sequenced using an Applied Biosystems 373A DNA Sequencer. Clones containing the correct DNA sequence for each of the four fragments were digested as before to release the fragments from the pSP72 vector. The Kpn I, Xho I-digested fragment C was ligated with the Xho I, Bgl II-digested fragment D and Kpn I, Bgl II-cut pSP72 in a three-way ligation The ligation products were then used to transform E. coli. Resulting transformants were sequenced and a clone of correct sequence obtained (designated CD). The 750 bp Bgl II Kpn I insert of CD was recleaved from the pSP72 vector and ligated with Bgl II, Sph I-digested fragment A and Sph I, Kpn I-digested fragment B in a three-way ligation as before except Bgl II was added to decrease undesired ligation products. The ligation products were separated on agarose gels, the 1.5 kbp fragment was isolated, and was designated D361-1.

Construction of HPV6/11 L1, HPV11 L1 and HPV6 L1 Yeast Expression Vectors—The pGAL1-10 yeast expression vector was constructed by isolating a 1.4 kbp SphI fragment from a pUC18/bidirectional GAL promoter plasmid which contains the *Saccharomyces cerevisiae* divergent GAL1-GAL10 promoters from the plasmid pBM272 (provided by Mark Johnston, Washington University, St. Louis, Mo.). The divergent promoters are flanked on each side by a copy of the yeast ADH1 transcriptional terminator (Bennetzen and Hall, 1982, *J. Biol. Chem.* 257: 3018–3025), a BamHI cloning site located between the GAL1 promoter and the first copy of the ADH1 transcriptional terminator and a SmaI cloning site located between the GAL10 promoter and the second copy of the ADH1 transcriptional terminator. A yeast shuttle vector consisting of pBR322, the yeast LEU2d gene (Erhart and Hollenberg, 1983, *J. Bacteriol* 156: 625–635) and the yeast 2u plasmid (gift of Benjamin Hall, University of Washington, Seattle, Wash.) (Broach and Volkert, 1991, Circular DNA Plasmids of Yeasts, Cold Spring Harbor Laboratory Press, Cold Spring Harbor, N.Y.) was digested with SphI and ligated with the 1.4 kbp SphI divergent GAL promoter fragment resulting in pGAL1-10.

The HPV6/11 hybrid L1 DNA encoding the HPV11 L1 protein (sample D361-1 from Example 1) contains a yeast non-translated leader sequence (Kniskern, et al., 1986, *Gene* 46: 135–141) immediately upstream to the HPV6/11 L1 initiating methionine codon. The pGAL1-10 plasmid was linearized with BamHI which cuts between the GAL1 promoter and the ADH1 transcription terminator and ligated with the 1.5 kbp, HPV6/11 L1 gene fragment (sample D361-1). E. coli DH5 (Gibco BRL, Inc.) transformants were screened and a pGAL1-10 plasmid containing the HPV6/11 L1 gene was isolated and designated as D362-1.

The wild-type HPV11 (wt-HPV11) DNA was cloned from a condyloma acuminatum lesion (kind gift of Dr. Darron Brown). Total human genomic DNA was extracted and digested with restriction endonucleases. The fraction containing wt-HPV11 DNA was ligated into an E. coli cloning vector to be used as a template for PCR. The wt-HPV11 L1 gene was amplified by PCR using Vent polymerase (New England Biolabs, Inc.), 10 cycles of amplification (94° C. 1 min, 48° C. 1 min, 72° C. 1 min 45 sec), and the following oligonucleotide primers which contain flanking Bgl II sites (underlined):

sense primer: 5'-CTC AGA TCT CAC AAA ACA AAA TGT GGC GGC CTA GCG ACA GCA CAG-3' (SEQ ID NO:29)

antisense primer: 5'-GAG AGA TCT TAC TTT TTG GTT TTG GTA CGT TTT CG-3' (SEQ ID NO:30)

The sense primer introduces a yeast non-translated leader sequence (Kniskern, et al., 1986, *Gene* 46: 135–141) immediately upstream to the wt-HPV11 L1 initiating methionine codon (highlighted in bold print). The 1.5 kbp wt-HPV11 L1 PCR product was digested with BglII, gel purified and ligated with the BamHI digested pGAL1-10 plasmid to yield plasmid, p329-1.

Total genomic DNA was extracted from an HPV6a-positive, condyloma acuminatum lesion (kind gift of Dr. Darron Brown). The HPV6a L1 gene was amplified by PCR using the biopsy sample DNA as a template, Vent polymerase (New England Biolabs, Inc.), 35 cycles of amplification (94° C. 1 min, 48° C. 1 min, 72° C. 1 min 45 sec), the sense primer listed above for PCR of wt-HPV11 L1 and an antisense primer with the sequence,

5'-GAG AGA TCT TAC CTT TTA GTT TTG GCG CGC TTA C-3' (SEQ ID NO:31).

The 1.5 kbp HPV6a L1 PCR product was digested with BglII, gel purified and ligated with the BamHI digested pGAL1-10 plasmid to yield plasmid D128.

Preparation of Strain 1558 a. Preparation of Yeast Strain U9

*Saccharomyces cerevisiae* strain 2150-2-3 (MATalpha, leu2-04, ade1, cir°) was obtained from Dr. Leland Hartwell (University of Washington, Seattle, Wash.). Cells of strain 2150-2-3 were propagated overnight at 30° C. in 5 mL of YEHD medium (Carty et al., 1987, *J. Ind Micro* 2: 117–121). The cells were washed 3 times in sterile, distilled water, resuspended in 2 mL of sterile distilled water, and 0.1 mL of cell suspension was plated onto each of six 5-fluoro-orotic acid (FOA) plates in order to select for ura3 mutants (Cold Spring Harbor Laboratory Manual for Yeast Genetics). The plates were incubated at 30° C. The medium contained per 250 mL distilled water: 3.5 g, Difco Yeast Nitrogen Base without amino acids and ammonium sulfate; 0.5 g 5-Fluoro-orotic acid; 25 mg Uracil; and 10.0 g Dextrose.

The medium was sterilized by filtration through 0.2 $\mu$m membranes and then mixed with 250 mL of 4% Bacto-Agar (Difco) maintained at 50° C., 10 mL of a 1.2 mg/mL solution of adenine, and 5 mL of L-leucine solution (180 mg/50 mL). The resulting medium was dispensed at 20 mL per petri dish.

After 5 days of incubation, numerous colonies had appeared. Single colonies were isolated by restreaking colonies from the initial FOA plates onto fresh FOA plates which were then incubated at 30° C. A number of colonies from the second set of FOA plates were tested for the presence of the ura3 mutation by replica-plating onto both YEHD plates and uracil-minus plates. The desired result was good growth on YEHD and no growth on uracil-minus medium. One isolate (U9) was obtained which showed these properties. It was stored as a frozen glycerol stock (strain #325) at −70° C. for later use.

b. Preparation of a Vector for disruption of the Yeast MNN9 gene—In order to prepare a vector for disruption of the MNN9 gene, it was necessary to first clone the MNN9 gene from S. cerevisiae genomic DNA. This was accomplished by standard Polymerase Chain Reaction (PCR) technology. A 5' sense primer and 3' antisense primer for PCR of the full-length MNN9 coding sequence were designed based on the published sequence for the yeast MNN9 gene (Zymogenetics: EPO Patent Application No. 88117834.7, Publication No. 0-314-09-A2). The following oligodeoxynucleotide primers containing flanking HindIII sites (underlined) were used:

sense primer: 5'-CTT AAA GCT TAT GTC ACT TTC TCT TGT ATC G-3' (SEQ ID NO:32);

antisense primer: 5'-TGA TAA GCT TGC TCA ATG GTT CTC TTC CTC-3' (SEQ ID NO:33).

The initiating methionine codon for the MNN9 gene is highlighted in bold print. The PCR was conducted using genomic DNA from *S. cerevisiae* strain JRY188 as template, Taq DNA polymerase (Perkin Elmer) and 25 cycles of amplification (94° C. 1 min., 37° C. 2 min., 72° C. 3 min.). The resulting 1.2 kbp PCR fragment was digested with HindIII, gel-purified, and ligated with HindIII-digested, alkaline-phosphatase treated pUC13 (Pharmacia). The resulting plasmid was designated p1183.

In order to disrupt the MNN9 gene with the yeast URA3 gene, the plasmid pBR322-URA3 (which contains the 1.1 Kbp HindIII fragment encoding the *S. cerevisiae* URA3 gene subcloned into the HindIII site of pBR322) was digested with HindIII and the 1.1 kbp DNA fragment bearing the functional URA3 gene was gel-purified, made blunt-ended with T4 DNA polymerase, and then ligated with PmlI-digested plasmid p1183 (PmlI cuts within the MN9 coding sequence). The resulting plasmid p1199 contains a disruption of the MNN9 gene by the functional URA3 gene.

c. Construction of U9-derivative strain 1372 containing disruption of MNN9 gene—For disruption of the MNN9 gene in strain U9 (#325), 30 μg of plasmid p1199 were digested with HindIII to create a linear mnn9::URA3 disruption cassette. Cells of strain 325 were transformed with the HindIII-digested p1199 DNA by the spheroplast method (Hinnen, et al., 1978, *Proc. Natl. Acad. Sci. USA* 75:1929–1933) and transformants were selected on a synthetic agar medium lacking uracil and containing 1.0 M sorbitol. The synthetic medium contained, per liter of distilled water: Agar, 20 g; Yeast nitrogen base w/o amino acids, 6.7 g; Adenine, 0.04 g; L-tyrosine, 0.05 g; Sorbitol, 182 g; Glucose, 20 g; and Leucine Minus Solution #2, 10 ml. Leucine Minus Solution #2 contains per liter of distilled water: L-arginine, 2 g; L-histidine, 1 g; L-Leucine, 6 g; L-Isoleucine, 6 g; L-lysine, 4 g, L-methionine, 1 g; L-phenylalanine, 6 g; L-threonine, 6 g; L-tryptophan, 4 g.

The plates were incubated at 30° C. for five days at which time numerous colonies had appeared. Chromosomal DNA preparations were made from 10 colonies and then digested with EcoRI plus HindIII. The DNA digests were then evaluated by Southern blots (Sambrook et al., 1989, *Molecular Cloning: A Laboratory Manual*, 2nd edition, Cold Spring Harbor Laboratory Press) using the 1.2 kbp HindIII fragment bearing the MNN9 gene (isolated from plasmid p1199) as a probe. An isolate was identified (strain #1372) which showed the expected DNA band shifts on the Southern blot as well as the extreme clumpiness typically shown by mnn9 mutants.

d. Construction of a Vector for Disruption of Yeast HIS3 Gene—In order to construct a disruption cassette in which the *S. cerevisiae* HIS3 gene is disrupted by the URA3 gene, the plasmid YEp6 (Struhl et al., 1979, *Proc. Natl. Acad. Sci. USA* 76:1035) was digested with BamHI and the 1.7 kbp BamHI fragment bearing the HIS3 gene was gel-purified, made blunt-ended with T4 DNA polymerase, and ligated with pUC18 which had been previously digested with BamHI and treated with T4 DNA polymerase. The resulting plasmid (designated p1501 or pUC18-HIS3) was digested with NheI (which cuts in the HIS3 coding sequence), and the vector fragment was gel-purified, made blunt-ended with T4 DNA polymerase, and then treated with calf intestine alkaline phosphatase. The URA3 gene was isolated from the plasmid pBR322-URA3 by digestion with HindIII and the 1.1 kbp fragment bearing the URA3 gene was gel-purified, made blunt-ended with T4 DNA polymerase, and ligated with the above pUC18-HIS3 NheI fragment. The resulting plasmid (designated pUC18-his3::URA3 or p1505) contains a disruption cassette in which the yeast HIS3 gene is disrupted by the functional URA3 gene.

e. Construction of Vector for Disruption of Yeast PRB1 Gene by the HIS3 Gene—Plasmid FP8ΔH bearing the *S. cerevisiae* PRB1 gene was provided by Dr. E. Jones of Carnegie-Mellon Univ. (Moehle et al., 1987, *Genetics* 115:255–263). It was digested with HindIII plus XhoI and the 3.2 kbp DNA fragment bearing the PRB1 gene was gel-purified and made bluntended by treatment with T4 DNA polymerase. The plasmid pUC18 was digested with BamHI, gel-purified and made blunt-ended by treatment with T4 DNA polymerase. The resulting vector fragment was ligated with the above PRB1 gene fragment to yield the plasmid pUC18-PRB1. Plasmid YEp6, which contains the HIS3 gene, was digested with BamHI. The resulting 1.7 kbp BamHI fragment bearing the functional HIS3 gene was gel-purified and then made blunt-ended by treatment with T4 DNA polymerase. Plasmid pUC18-PRB1 was digested with EcoRV plus NcoI which cut within the PRB1 coding sequence and removes the protease B active site and flanking sequence. The 5.7 kbp EcoRV-NcoI fragment bearing the residual 5' and 3'-portions of the PRB1 coding sequence in pUC18 was gel-purified, made blunt-ended by treatment with T4 DNA polymerase, dephosphorylated with calf intestine alkaline phosphatase, and ligated with the blunt-ended HIS3 fragment described above. The resulting plasmid (designated pUC18-prb1::HIS3, stock #1245) contains the functional HIS3 gene in place of the portion of the PRB1 gene which had been deleted above.

f. Construction of a U9-related Yeast Strain containing disruptions of both the MNN9 and PRB1 Genes—The U9-related strain 1372 which contains a MNN9 gene disruption was herein. Clonal isolates of strain 1372 were passaged on FOA plates to select ura3 mutants. A number of ura3 isolates of strain 1372 were obtained and one particular isolate (strain 12930-190-S1-1) was selected for subsequent disruption of the HIS3 gene. The pUC18-his3::URA3 gene disruption vector (p1505) was digested with XbaI plus EcoRI to generate a linear his3::URA3 disruption cassette and used for transformation of strain 12930-190-S1-1 by the lithium acetate method (Methods in Enzymology, 1992, 194:290). Ura$^+$ transformants were selected on synthetic agar medium lacking uracil, restreaked for clonal isolates on the same medium, and then replica-plated onto medium lacking either uracil or histidine to screen for those isolates that were both Ura$^+$ and His$^-$. One isolate (strain 12930-230-1) was selected for subsequent disruption of the PRB1 gene. The PRB1 gene disruption vector (pUC18-prb1::HIS3, stock #1245) was digested with SacI plus XbaI to generate a linear prb1::HIS3 disruption cassette and used for transformation of strain 12930-230-1 by the lithium acetate method. His$^+$ transformants were selected on agar medium lacking histidine and restreaked on the same medium for clonal isolates. Genomic DNA was prepared from a number of the resulting His$^+$ isolates, digested with EcoRI, and then electrophoresed on 0.8% agarose gels. Southern blot analyses were then performed using a radio-labeled 617 bp probe for the PRB1 gene which had been prepared by PCR using the following oligodeoxynucleotide primers:

5'-TGG TCA TCC CAA ATC TTG AAA-3' (SEQ ID NO:34); and

5'-CAC CGT AGT GTT TGG AAG CGA-3' (SEQ ID NO:35)

Eleven isolates were obtained which showed the expected hybridization of the probe with a 2.44 kbp prb1::HIS3 DNA fragment. This was in contrast to hybridization of the probe with the 1.59 kbp fragment for the wild-type PRB1 gene. One of these isolates containing the desired prb1::HIS3 disruption was selected for further use and was designated strain #1558.

EXAMPLE 2

Expression of HPV11 L1 and HPV6 L1 in Yeast—Plasmids D362-1 (pGAL1–10+HPV6/11 L1), p329-1 (pGAL1–10+wt-HPV11 L1), D128 (pGAL1–10+HPV6 L1) and pGAL1–10 were used to transform S. cerevisiae strain #1558 (MATa, leu2-04, prb1::HIS3, mnn9::URA3, ade1, ciro) by the spheroplast method (Hinnen et al., 1978, Proc. Natl. Acad. Sci. USA 75, 1929–1933). The #1558 yeast strain transformed with plasmid D362-1 was designated as strain #1782. For RNA studies, yeast clonal isolates were grown at 30° C. in YEH complex medium (Carty et al., 1987, J. Ind. Micro. 2, 117–121) containing 0.1 M sorbitol and either 2% glucose or galactose for 26 hours. After harvesting the cells, yeast RNA was extracted using the hot acidic phenol method as described (Current Protocols in Molecular Biology, vol. 2, Current Protocols, 1993). For protein analysis, the identical isolates were grown at 30° C. in YEH complex medium containing 0.1 M sorbitol, 2% glucose and 2% galactose for 70 hours. After harvesting the cells, the cell pellets were broken with glass beads and cell lysates analyzed for the expression of HPV11 L1 or HPV6 L1 protein by immunoblot analysis.

Fermentation of HPV6/11 L1 (Strain #1782)—Surface growth of a plate culture of strain 1782 was aseptically transferred to a leucine-free liquid medium containing (per L): 8.5 g Difco yeast nitrogen base without amino acids and ammonium sulfate; 0.2 g adenine; 0.2 g uracil; 10 g succinic acid; 5 g ammonium sulfate; and 0.25 g L tyrosine; this medium was adjusted to pH 5.0–5.3 with NaOH prior to sterilization. After growth for 25 hr at 28° C., 250 rpm on a rotary shaker, frozen culture vials were prepared by adding sterile glycerol to a final concentration of 17% (w/v) prior to storage at −70 C (1 mL per cryovial). Inoculum for fermentation of strain 1782 was developed in the same medium (750 mL per 2-L flask) and was started by transferring the thawed contents of two frozen culture vials to the 2-L flasks and incubating at 28° C., 250 rpm on a rotary shaker for 25 hr. Fermentation of strain 1782 used a Chemap 23 L fermenter with a working volume of 18 L after inoculation. The production medium used contained (per L): 20 g Difco yeast extract; 10 g Sheffield HySoy peptone; 20 g glucose; 20 g galactose; the medium was adjusted to pH 5.3 prior to sterilization. The entire contents (500 mL) of the 2-L inoculum flask was transferred to the fermenter which was incubated at 28° C., 9 L air per min, 500 rpm, 3.5 psi pressure. Agitation was increased as needed to maintain dissolved oxygen levels of greater than 40% of saturation. Progress of the fermentation was monitored by offline glucose measurements (Beckman Glucose 2 Analyzer) and online mass spectrometry (Perkin-Elmer 1200). After 66 hr incubation, a cell density of 9.32 g dry cell weight per L was reached. The contents of two such fermentations (total 17.5 L broth) were pooled before cell recovery. The culture was concentrated by hollow fiber filtration (Amicon H5MP01-43 cartridge in an Amicon DC-10 filtration system) to ca. 2 L, diafiltered with 2 L phosphate-buffered saline, and concentrated further (to ca. 1 L) before dispensing into 500 mL centrifuge bottles. Cell pellets were collected by centrifugation at 8,000 rpm (Sorval GS3 rotor) for 20 min at 4° C. After decanting the supernatant, the pellets (total 358 g wet cells) were stored at −70° C. until use.

Purification of Recombinant HPV Type 11 L1 Capsid Proteins—All steps were performed at 4° C. unless noted. Cells were stored frozen at −70° C. Frozen cells (wet weight=180 g) were thawed at 20–23° C. and resuspended in 900 mL "Breaking Buffer" (50 mM MOPS, pH 7.2, 500 mM NaCl, 1 mM $CaCl_2$). The protease inhibitors AEBSF and pepstatin A were added to final concentrations of 1 mM and 1.7 mM, respectively. The cell slurry was broken at a pressure of approximately 16,000 psi by 4 passes in a M110-Y Microfluidizer (Microfluidics Corp., Newton, Mass.). A sufficient volume of 10% Triton X100® detergent (Pierce, Rockford, Ill.) was added to the broken cell slurry to bring the concentration of TX100 to 0.5%. The slurry was stirred for 20 hours. The Triton X100-treated lysate was centrifuged at 12,000×g for 40 min to remove cellular debris. The supernatant liquid containing L1 protein was recovered.

The supernatant liquid was diafiltered against five volumes of 20 mM sodium phosphate, pH 7.2, 0.5 M NaCl using a 300K tangential flow membrane cassette (Filtron, Northborough, Mass.). The material retained by the membrane was shown by radioimmunoassay and western blotting to contain the L1 protein.

The retentate was applied to a high resolution affinity column (11.0 cm ID×5.3 cm) of SP Spherodex (M)® resin (IBF, Villeneuve-la-Garenne, France) equilibrated in 20 mM sodium phosphate, pH 7.2, 0.5 M NaCl. Following a wash with equilibration buffer and a step wash with 20 mM sodium phosphate, pH 7.2, 1.0 M NaCl, the L1 protein was eluted with a step wash of 20 mM sodium phosphate, pH 7.2, 2.5 M NaCl. Fractions were collected during the washes and elution. Column fractions were assayed for total protein by the Bradford method. Fractions were then analyzed by western blotting and SDS-PAGE with colloidal Coomassie detection. Fractions were also analyzed by radioimmunoassay.

SP Spherodex fractions showing comparable purity and enrichment of L1 protein were pooled. The final product was analyzed by western blotting and SDS-PAGE with colloidal Coomassie detection. The L1 protein was estimated to be >90% homogeneous. The identity of L1 protein was confirmed by western blotting. The final product was filtered aseptically through a 0.22 mm membrane and stored at −70° C. in 50 mM MOPS and 1.25 M NaCl.

Electron microscopy analysis is performed by Structure Probe (West Chester, Pa.). An aliquot of sample is placed on a 200 mesh carbon-coated copper grid. A drop of 2% phosphotungstic acid, pH 7.0 is placed on the grid for 20 seconds. The grid is allowed to air dry prior to TEM examination. All microscopy is performed using a JEOL 100 CX transmission electron microscope (JEOL USA, Inc.) at an accelerating voltage of 100 kV. The micrographs generated have a final magnification of 100,000×.

Bradford Assay for Total Protein—Total protein was assayed using a commercially available Coomassie Plus® kit (Pierce, Rockford, Ill.). Samples were diluted to appropriate levels in Milli-Q-$H_2O$. Volumes required were 0.1 mL and 1.0 mL for the standard and microassay protocols, respectively. For both protocols, BSA (Pierce, Rockford, Ill.) was used to generate the standard curve. Assay was performed according to manufacturer's recommendations. Standard curves were plotted using CricketGraph® software on a Macintosh IIci computer.

SDS-PAGE and Western Blot Assays—All gels, buffers, and electrophoretic apparatus were obtained from Novex (San Diego, Calif.) and were run according to manufacturer's recommendations. Briefly, samples were diluted to equal protein concentrations in Milli-Q-H$_2$O and mixed 1:1 with sample incubation buffer containing 200 mM DTT. Samples were incubated 15 min at 100° C. and loaded onto pre-cast 12% Tris-glycine gels. The samples were electrophoresed at 125V for 1 hr 45 min. Gels were developed by colloidal Coomassie staining using a commercially obtained kit (Integrated Separation Systems, Natick, Mass.).

For western blots, proteins were transferred to PVDF membranes at 25V for 40 min. Membranes were washed with Milli-Q-H$_2$O and air-dried. Primary antibody was polyclonal rabbit antiserum raised against a TrpE-HPV11L1 fusion protein (gift of Dr. D. Brown). The antibody solution was prepared by dilution of antiserum in blotting buffer (5% non-fat milk in 6.25 mM Na phosphate, pH 7.2, 150 mM NaCl, 0.02% NaN$_3$). Incubation was for at least 1 hour at 20–23° C. The blot was washed for 1 min each in three changes of PBS (6.25 mM Na phosphate, pH 7.2, 150 mM NaCl). Secondary antibody solution was prepared by diluting goat anti-rabbit IgG alkaline phosphatase-linked conjugate antiserum (Pierce, Rockford, Ill.) in blotting buffer. Incubation proceeded under the same conditions for at least 1 hour. Blots were washed as before and detected using a 1 step NBT/BCIP substrate (Pierce, Rockford, Ill.).

EXAMPLE 3

PROTEIN CONCENTRATION DEPENDENCE OF AGGREGATION

A lot of HPV11 VLP was prepared as described above and was stored at 0.47 mg/mL in 50 mM MOPS containing 1.25 M NaCl. This lot was thawed and a portion of this solution was diluted to 18 mcg/mL in the same buffer. While the stock solution at higher protein concentration maintained the same hydrodynamic diameter (D$_h$), in the range of 107–115 nm (as measured by dynamic light scattering), for 2 months at 4° C., the lower protein concentration solution aggregated over time even though the salt concentration was maintained at 1.25 M NaCl (FIG. 1). FIG. 1 shows that at lower HPV protein concentration, even high concentrations of salt do not protect HPV from aggregation during storage at 4° C.

EXAMPLE 4

SALT CONCENTRATION DEPENDENCE OF AGGREGATION

Figure 2:
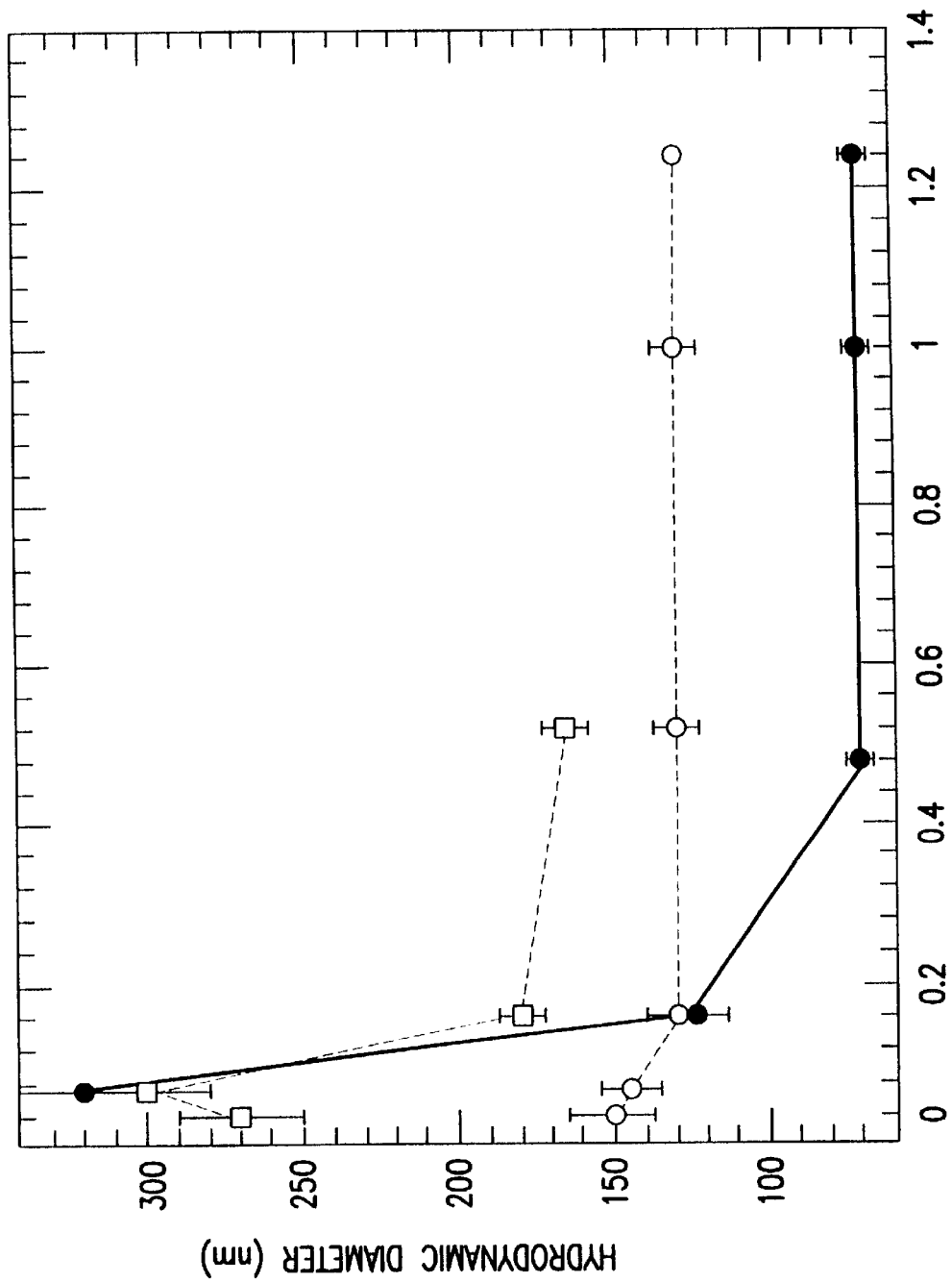
FIG. 2 shows the effect of salt concentration on HPV 11 and HPV 16 L1 VLP hydrodynamic size during storage at room temperature. Samples were diluted into a buffer, stored for one hour and then analyzed. In the case of HPV 11, samples were then also dialyzed overnight against the same buffer. The HPV 11 L1 VLP was formulated in 50 mM MOPS buffer (pH 7.0) containing different NaCl concentrations, (○) no dialysis; (□) dialysis. The HPV 16 L1 VLP was formulated in 50 mM MOPS buffer (pH 7.0) containing different NaCl concentrations, (●) no dialysis.

A lot of HPV11 and HPV 16 VLP was prepared and was tested for salt dependence of hydrodynamic size during storage. Recombinant HPV 11 and 16 VLP was diluted from the stock solution (in 50 mM MOPS, 1.25 M NaCl, pH 7.0) into 50 mM MOPS buffer such that the final protein concentration remained constant at about 20 mcg/mL, but the NaCl concentration varied as indicated in FIG. 2. The dilutions were made in polypropylene eppendorf tubes and stored at room temperature. Measurements were made within one hour of preparing the dilutions because, as indicated in the previous example (FIG. 1), a slow aggregation occurs at this protein concentration even in a solution containing high salt concentration. The D$_h$ value was nearly invariant down to 0.15 M NaCl (HPV 11) and 0.5M NaCl (HPV 16), but increased at a lower salt concentrations (FIG. 2). On the other hand, dialyzed samples of HPV 11 manifested larger hydrodynamic sizes at all salt concentrations, and the effect was especially pronounced at salt concentrations below 0.5 M NaCl.

A separate experiment with a different lot of HPV11 (data not shown in figure form) shows that recombinant HPV 11 L1 VLP (dialyzed into 20 mM sodium phosphate buffer (pH 7.2) containing different NaCl concentrations) manifested an increase in Dh from approximately 113 nm in 0.5 M NaCl to 133 nm in 0.15 M NaCl. Samples dialyzed into 1.0, 2.0 and 3.0 M NaCl manifested Dh values of 114, 113 and 108 nm in a head-to-head comparison, while a sample dialyzed into a NaCl concentration of 0.025 M formed a visible precipitate. The protein concentrations of these samples were in the range of 130–179 mcg/mL (as measured by the Lowry protein assay) except for the sample in 0.025 M NaCl which had only 16 mcg/mL protein remaining in solution. A control sample, which was stored in 20 mM sodium phosphate buffer (pH 7.2) containing 2.5 M NaCl but not dialyzed, yielded a Dh value of 82 nm.

The data of this Example show that while low salt concentrations or low ionic strengths are conducive to inter-particle aggregation of HPV VLP's, low protein concentrations and physical manipulations of the HPV solution (such as dialysis of the protein) are also major contributors to HPV VLP aggregation.

EXAMPLE 5

SURFACE ADSORPTION OF HPV 11 VLPs

Figure 3:
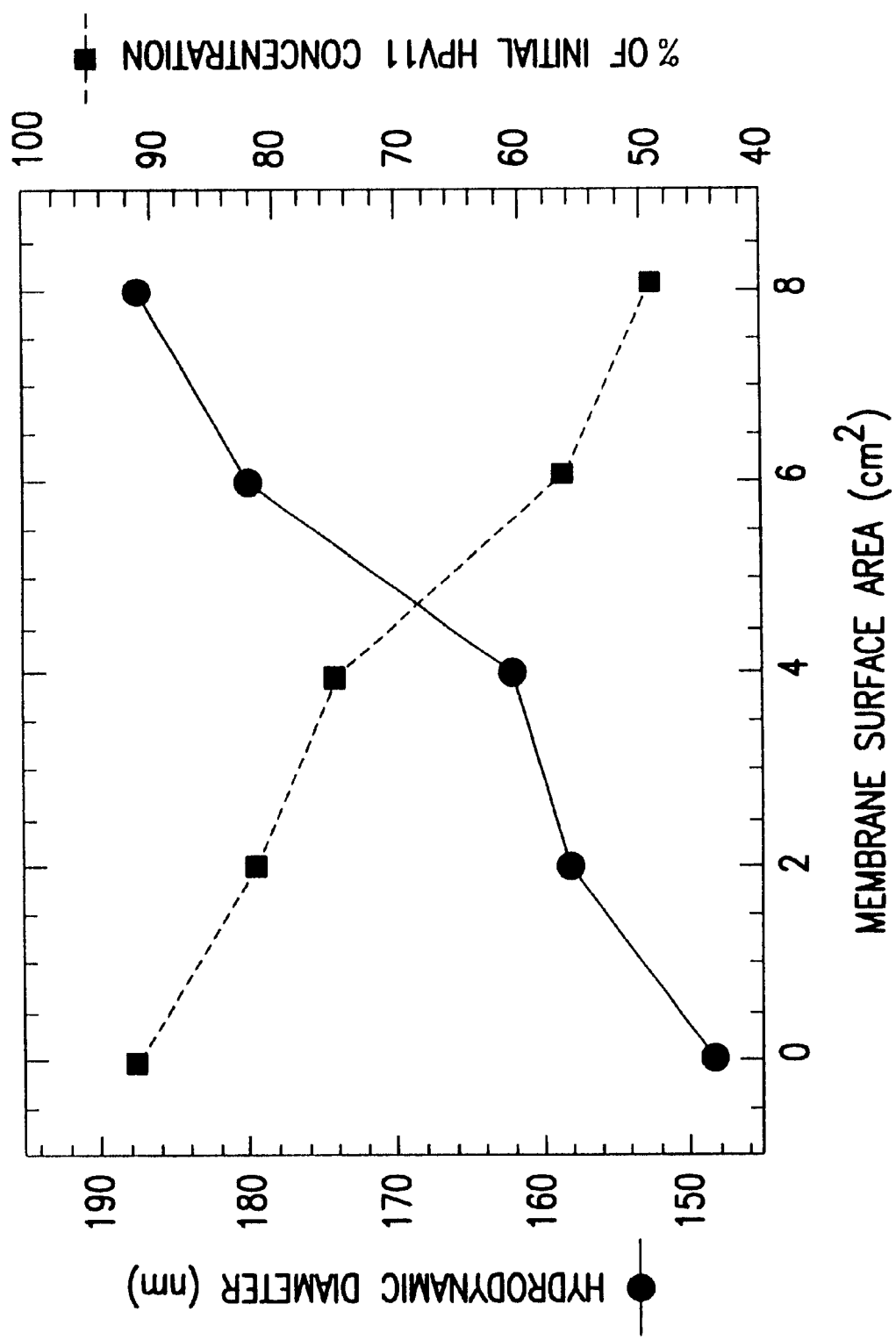
FIG. 3 shows the effect of protein adsorption to a dialysis membrane on hydrodynamic size (●) and protein concentration (■) [as a percentage of HPV 11 L1 remaining] of 50 mcg/ml of HPV 11 L1 VLP in 50 mM MOPS, pH 7.0 at 180 mM NaCl in a polypropylene tube at room temperature for 96 hours.

Dialysis membrane surface—A 50 mcg/mL solution of the protein in 50 mM MOPS buffer at pH 7.0 containing 0.18 M NaCl was incubated with different surface areas of the dialysis membrane in order to examine the effect of the dialysis membrane directly on HPV 11 aggregation. The Dh was found to increase with increasing surface area of the membrane after 96 hours of incubation at room temperature (FIG. 3). Concomitantly, the protein concentration in solution was found to decrease with increasing membrane surface area (FIG. 3). These observations indicate adsorption of HPV 11 on the membrane surface and suggest a correlation between surface adsorption and aggregation. These data show that prolonged exposure of low concentrations of HPV to polypropylene surface and dialysis membrane surface cause surface adsorption and aggregation. Both of these processes are temperature dependent. Samples incubated at 4° C. manifested a slower kinetics for both processes than those at 25° C.

Figure 4:
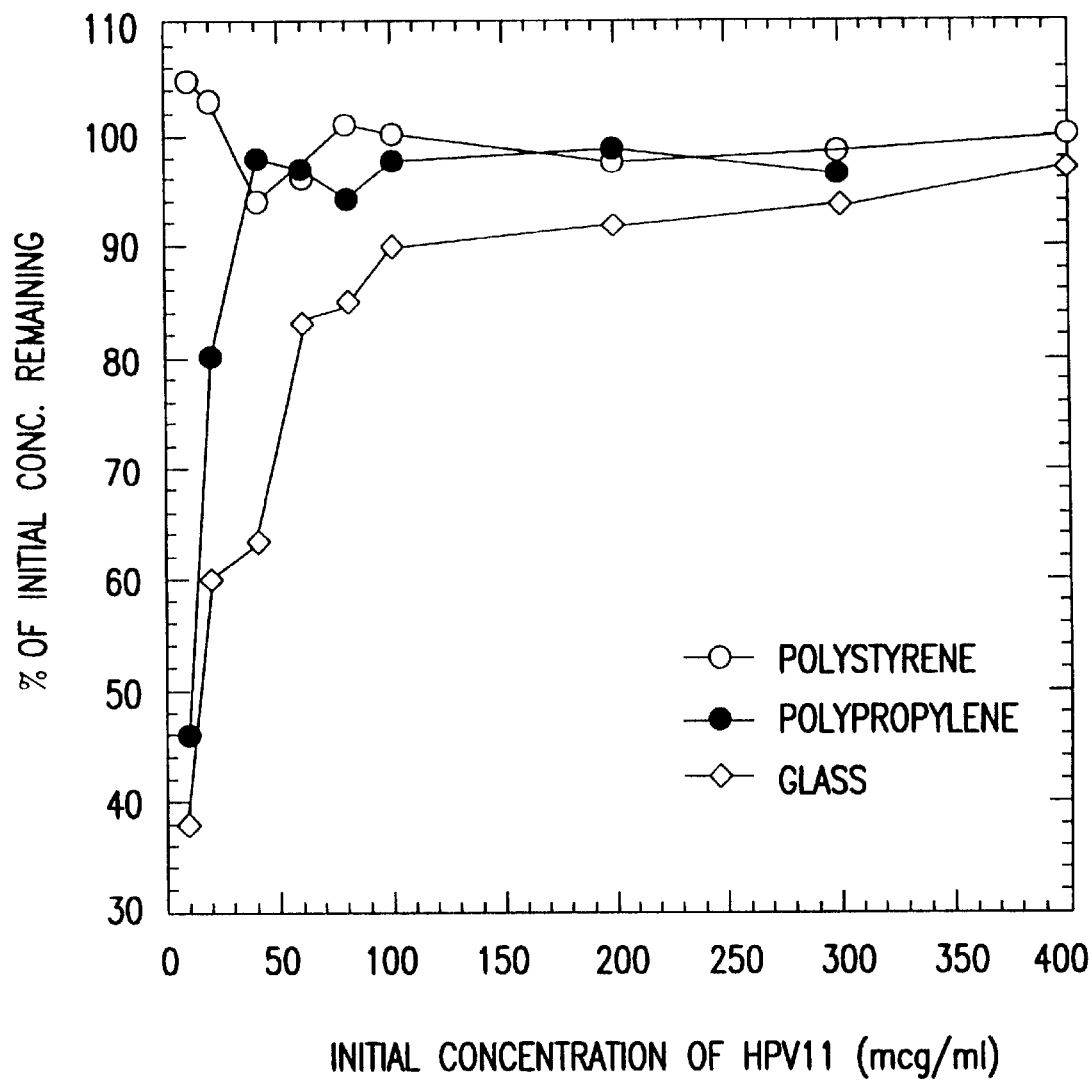
FIG. 4 shows the effect of polystyerene (○), polypropylene (●), and glass (◇) on HPV 11 L1 VLP adsorption in 50 mM MOPS, pH 7.0 at 1.25 M NaCl at room temperature for 24 hours.

Comparison of HPV adsorption on different container surfaces—HPV adsorption was compared, at identical surface to volume ratios, in borosilicate glass, polypropylene and polystyrene tubes (identical dimensions of 12×75 mm$^2$) at various HPV concentrations. Samples were incubated in 50 mM MOPS buffer containing 1.25 M NaCl at pH 7.0 and left at room temperature for 24 hours. FIG. 4 shows that surface adsorption is significant in borosilicate glass below 100 mcg/mL. Polypropylene fares better in that adsorption becomes a significant problem below 30 mcg/mL, but not at higher concentrations under these conditions. Polystyrene performs the best and does not show any significant protein adsorption down to 10 mcg/mL.

Figure 5:
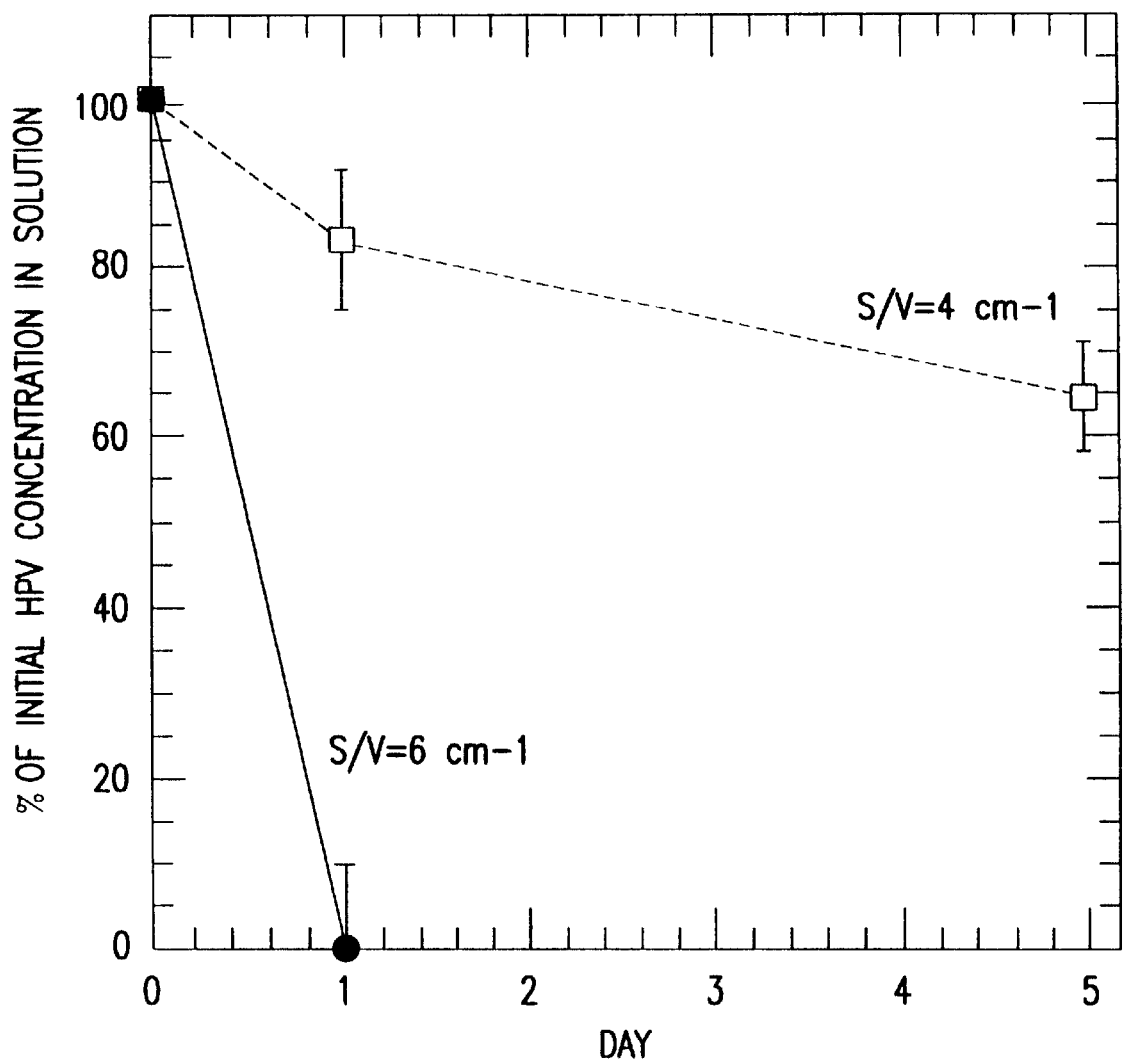
FIG. 5 shows the effect of increasing the surface/volume ratio on HPV L1 VLP (18 mcg/L) adsorption to polypropylene in 50 mM MOPS, pH 7.0, 0.25 M NaCl. (□) surface/volume=4 cm$^{-1}$; (●) surface/volume=6 cm$^{-1}$.

The surface adsorption of HPV was examined further where HPV 11(18 mcg/mL in 50 mM MOPS buffer containing 0.25 M NaCl) was placed in polypropylene tubes at two different surface to volume ratios (FIG. 5). After one day at room temperature, essentially all of the HPV was surface adsorbed at a surface to volume ratio of 6.0 cm$^{-1}$, while approximately 15% adsorption was seen when the surface to volume ratio was 4.0 cm$^{-1}$ (FIG. 5).

EXAMPLE 6

EXCIPIENTS INHIBITING HPV11 VLP SURFACE ADSORPTION AND AGGREGATION

Figure 6A:
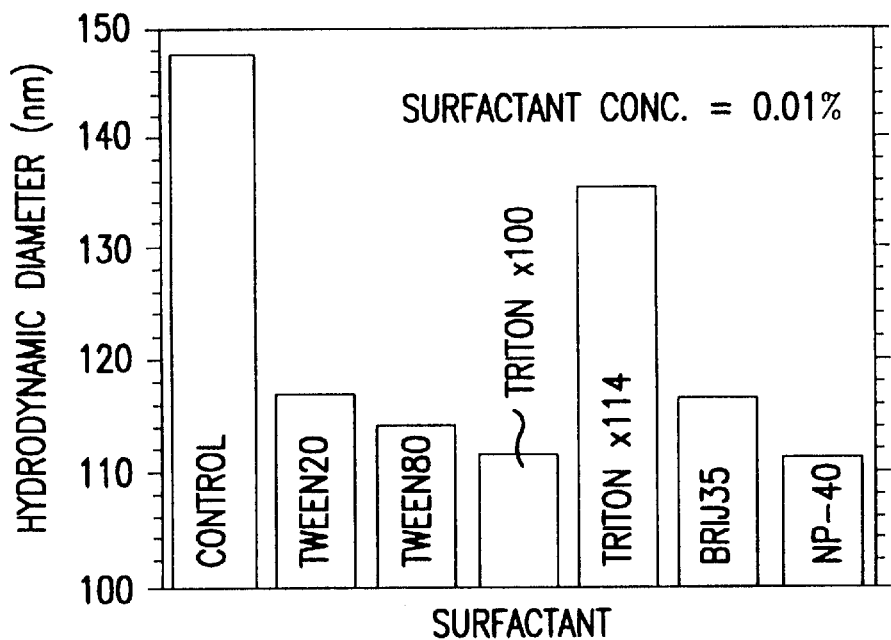
FIG. 6A and FIG. 6B show the effect of various surfactants (at 0.01%) on the stability of HFV 11 L1 VLP (18 mcg/mL) in 50 mM MOPS, pH 7.0, 150 mM NaCl at room temperature for 20 hours (Panel A) and in 50 mM MOPS, pH 7.0, 40 mM NaCl at 50° C. for 30 minutes and then to room temperature for 48 hours (Panel B) before being subjected to dynamic light scattering (DLS).

Screening of surfactants in an accelerated stability experiment—In a preliminary screening experiment, HPV 11 samples, in the presence and absence of 0.01% of several surfactants, were incubated at room temperature for 20 hours. HPV concentration was 18 mcg/mL and the buffer contained 50 mM MOPS, 0.15 M NaCl at pH 7.0. Several surfactants offered partial protection against aggregation under these conditions compared to the surfactant-untreated HPV sample, as determined by dynamic light scattering (FIG. 6A).

Figure 6B:
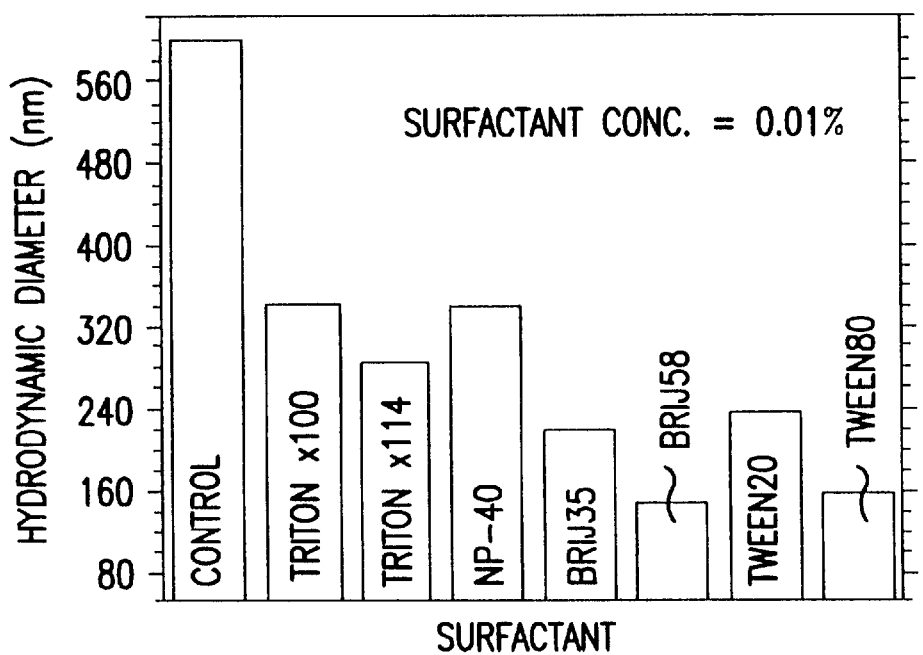

A surfactant screening experiment was performed under a more stressed condition. HPV 11 was incubated in the absence or presence of 0.01% of each surfactant at 50° C. for 30 minutes, and then at room temperature for 2 days. HPV concentration was 18 mcg/mL and the buffer contained 50 mM MOPS and 0.04 M NaCl at pH 7.0. Under these conditions, the surfactant-untreated control HPV sample aggregated to a much greater degree compared to the experiment described above. Of the surfactants tested, FIG. 6B shows that polyoxyethylene sorbitan fatty acid esters (Tween 80®) and polyoxyethylene alkyl ethers (Brij 58®) provided the best protection from HPV11 VLP aggregation.

Figure 7A:
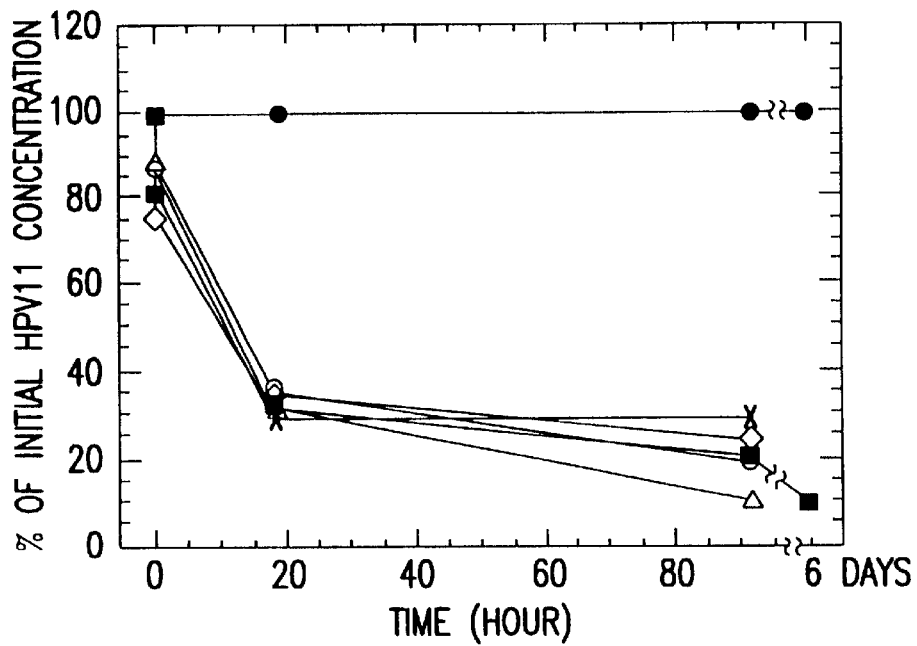
FIGS. 7A and 7B show the effect of Polysorbate 80 (e.g., Tween 80®) on surface adsorption (Panel A) and aggregation (Panel B) of HPV 11 L1 VLP (16 mcg/mL) against a polypropylene surface at room temperature in 50 mM MOPS, pH 7.0, at various ionic strengths: (●) 0.4 M $(NH_4)_2SO_4$+0.01% Tween 80®; (○) 0.1 M $(NH_4)_2SO_4$; (◇) 0.5 M $(NH_4)_2SO_4$; (x) 0.1 M $Na_2SO_4$; (|) 0.5 M $Na_2SO_4$; (Δ) 0.1 M NaCl; and, (■) 0.5 M NaCl.
Figure 7B:
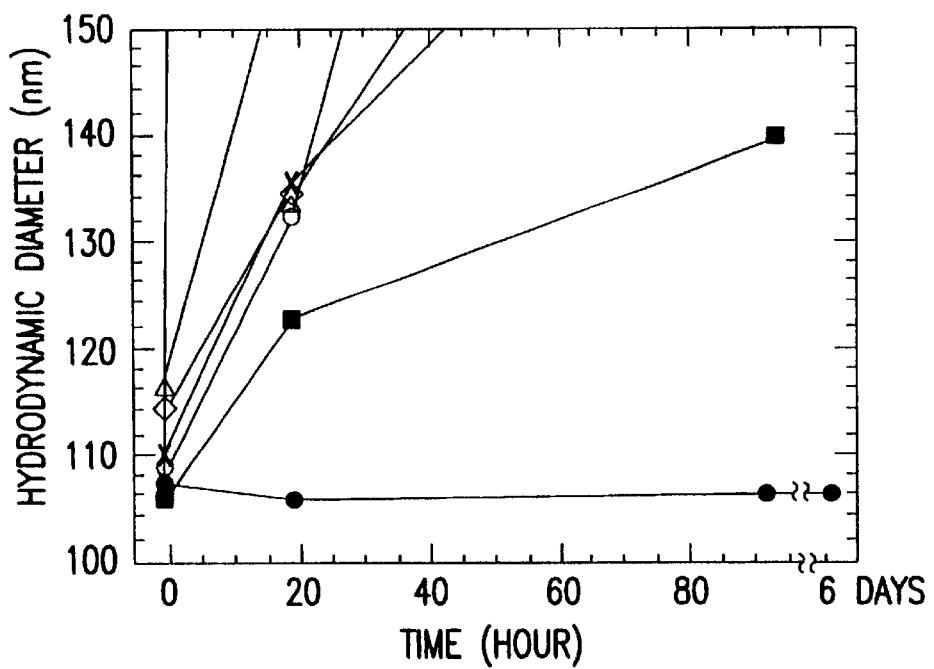

Protective effect of salt and Polysorbate 80 in combination—FIG. 7A and FIG. 7B show that at lower HPV concentrations high salt concentrations alone do not prevent HPV VLP surface adsorption or aggregation for sodium chloride, sodium sulfate and ammonium sulfate each at 0.1 M and 0.5 M. Conversely, FIG. 7A and FIG. 7B also show that addition of the non-ionic surfactant Tween 80® to a 0.4 M ammonium sulfate containing buffer results in almost complete protection against adsorption and aggregation even after 6 days at room temperature.

Figure 8:
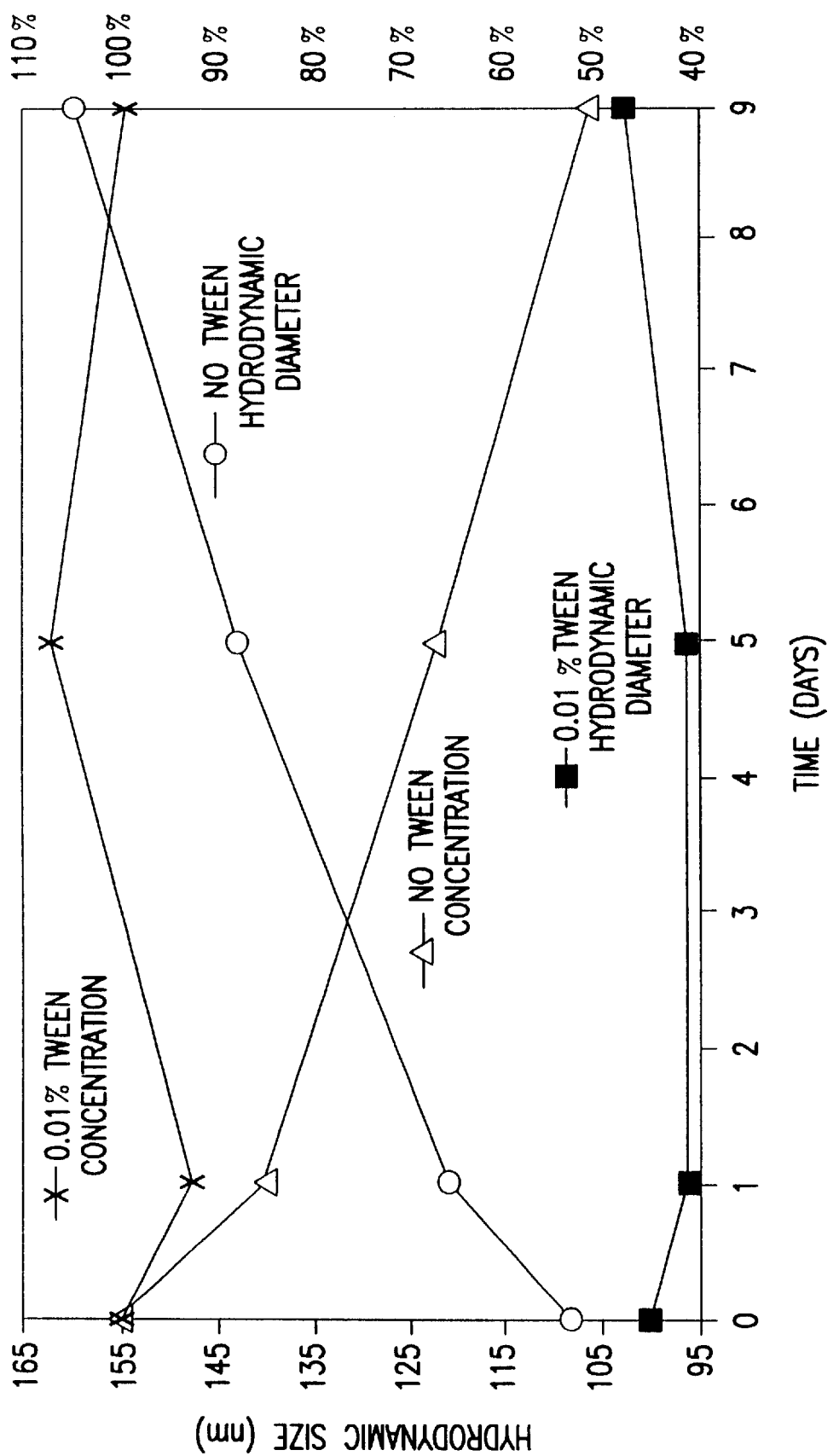
FIG. 8 shows the effect of of Polysorbate 80 (e.g., Tween 80®) on both hydrodynamic diameter and HPV 11 L1 VLP concentration of HPV 11 L1 VLP (18 mcg/mL) against a polypropylene surface in 50 mM MOPS, pH 7.0, 250 mM NaCl at room temperature over time. Protein concentration is measured as a percentage of the initial protein concentration. Decrease in protein concentration is inversely related to surface adsorption. (x) 0.01% Tween 80®, protein concentration; (Δ) no Tween 80®, protein concentration; (■) 0.01% Tween 80®, hydrodynamic diameter; and, (♦) no Tween 80®, hydrodynamic diameter.

The effect of Polysorbate 80 (e.g., Tween 80®) and NaCl on surface adsorption and aggregation was reconfirmed in a separate experiment. HPV 11 L1 VLP, at a concentration of 18 mcg/mL, was incubated in polypropylene tubes in 50 mM MOPS buffer containing 250 mM NaCl at pH 7 with or without 0.01% Tween 80®. FIG. 8 shows the percentage of protein adsorbed and Dh values as a function of incubation time at room temperature. In the absence of Tween 80®, both adsorptive loss and aggregation are very significant, while 0.01% Tween 80® provides protection against both problems.

Figure 9:
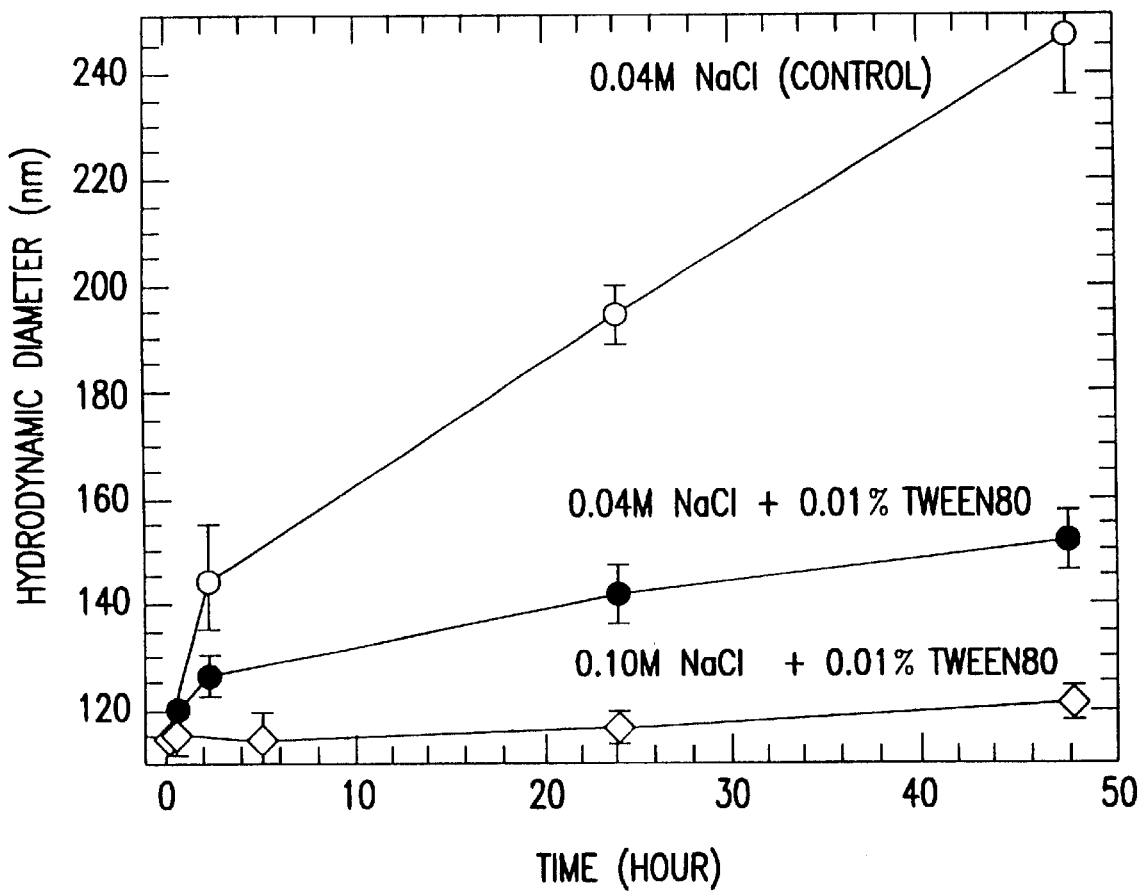
FIG. 9 shows the combined effect of NaCl concentration and of Polysorbate 80 (e.g., Tween 80®) on hydrodynamic size for HPV 11 L1 VLP (18 mcg/mL) in 50 mM MOPS, pH 7.0, with (●) 40 mM NaCl and 0.01% Tween 80®; (◇) 100 mM NaCl and 0.01% Tween 80®; and (○) 40 mM NaCl, absent Tween 80®.

FIG. 9 shows that an optimal salt concentration is required, in addition to Polysorbate 80, to protect low concentrations of HPV 11 VLPs (100 mcg/mL) from aggregation and adsorption. Also, it can be seen that an increase in Tween 80® in formulations with a low ionic strength offers partial but not full protection. FIG. 9 shows that aggregation of HPV 11 (18 mcg/mL) was only partially controlled by 0.01% Tween 80® in a buffer containing 50 mM MOPS and 0.04 M NaCl, but was almost totally protective against VLP aggregation for 48 hours at room temperature when the NaCl concentration was increased to 0.10 M.

Figure 10A:
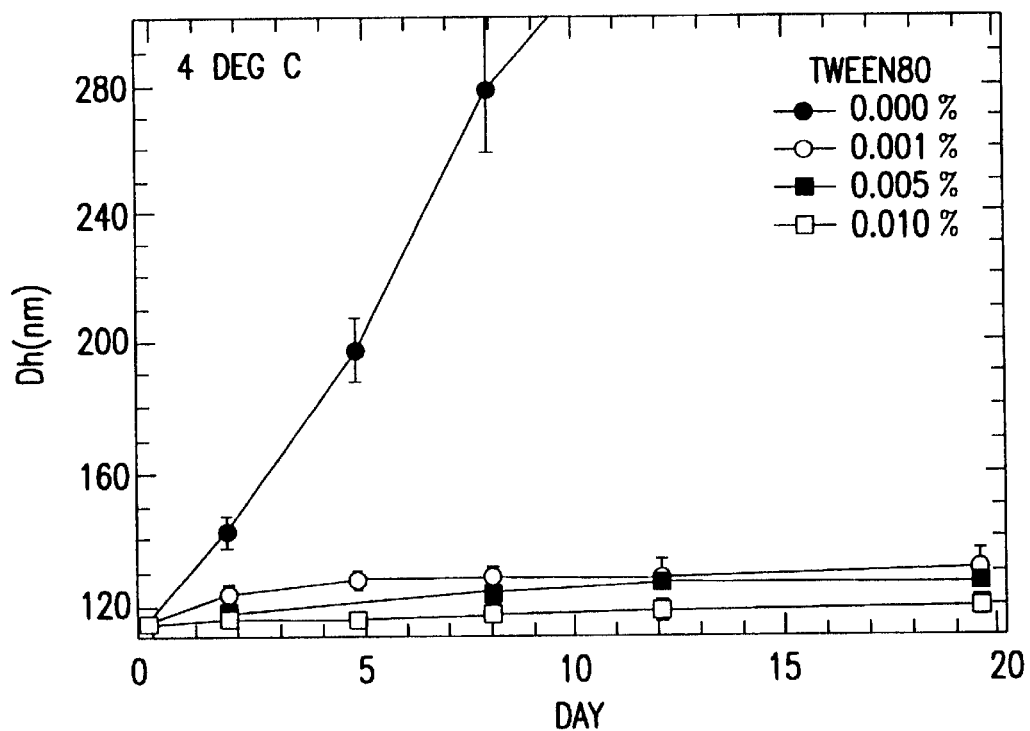
FIG. 10A and FIG. 10B show the effect of of Polysorbate 80 (e.g., Tween 80®) concentration [(●) 0.000% w/v; (○) 0.001% w/v; (■) 0.005% w/v; (□) 0.010% w/v] on hydrodynamic size (Dh (nm)) for HPV 11 L1 VLP (18 mcg/mL) in 50 mM MOPS, pH 7.0, 150 mM NaCl at 4° C. (Panel A) and room temperature (Panel B) over time.
Figure 10B:
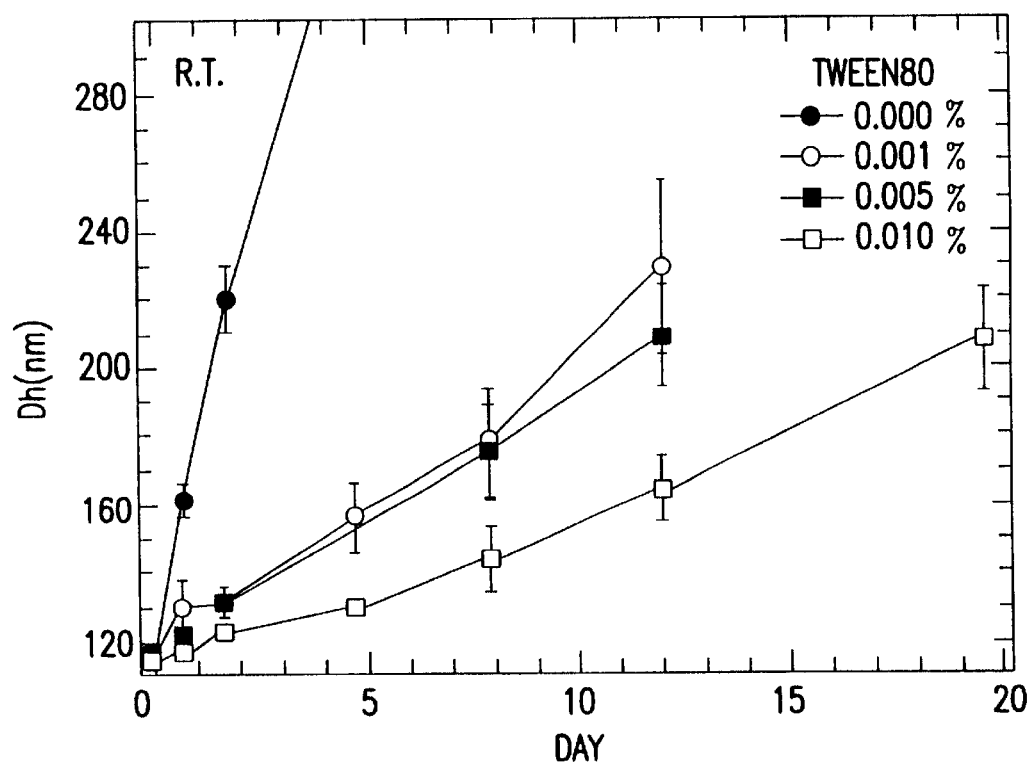

FIG. 10 shows the effect of titrating Polysorbate 80 on HPV 11 VLP (18 mcg/mL) aggregation in 50 mM MOPS buffer containing 0.15 M NaCl at pH 7.0. Samples were incubated with Tween 80® concentrations ranging from 0 to 0.01% at 4° C. and room temperature. At 4° C., no significant aggregation has been observed up to 20 days in the 0.01% Tween containing sample, while partial protection against aggregation is observed at room temperature.

Figure 11:
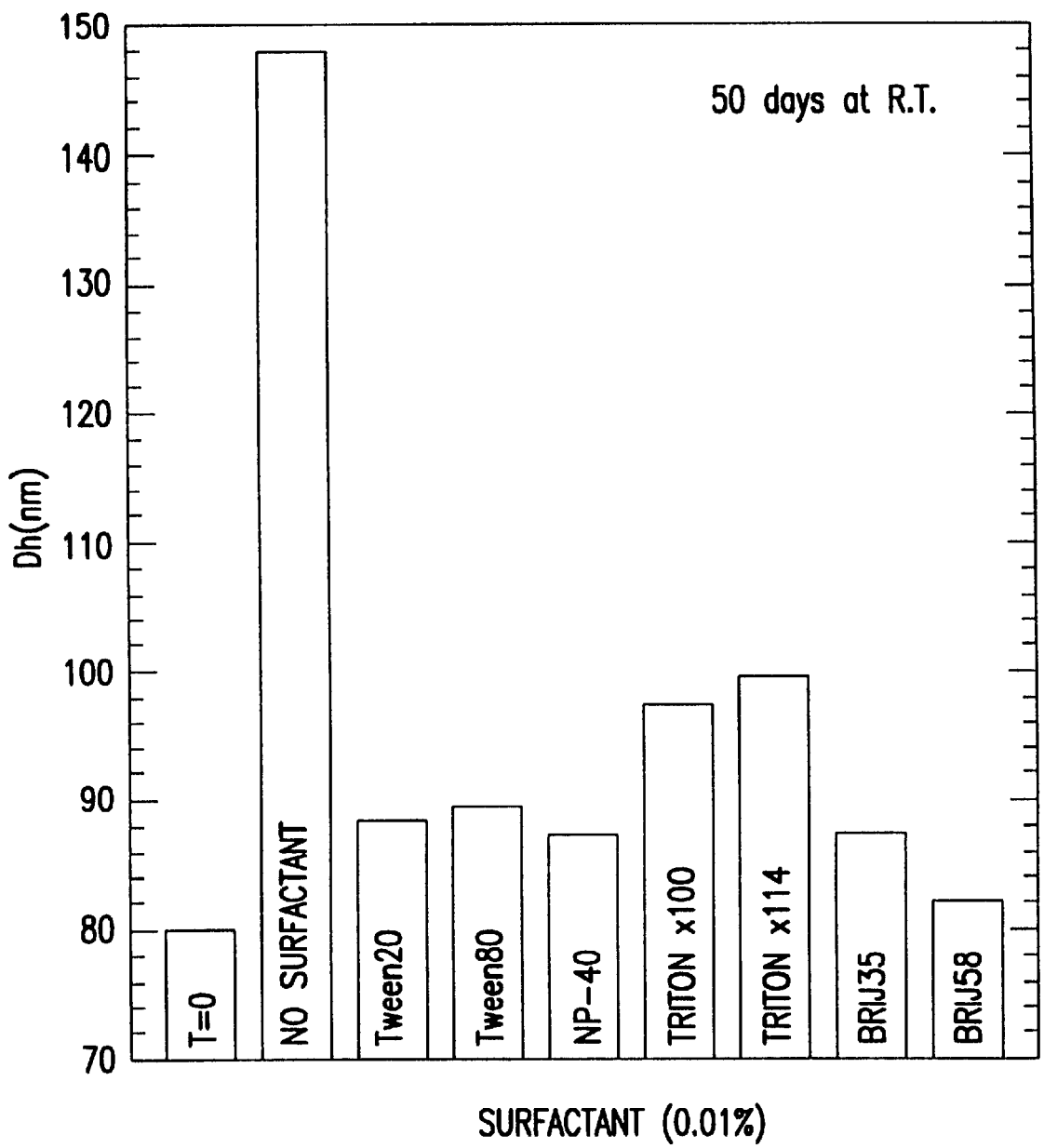
FIG. 11 shows the effect of various surfactants (at 0.01%) on the stability of HPV 16 L1 VLP (20 mcg/mL) stored in 50 mM MOPS, pH 7.0, 150 mM NaCl at room temperature for 50 days before being subjected to dynamic light scattering (DLS).

FIG. 11 shows the ability of nonionic surfactants to protect HPV 16 VLP against aggregation. The surfactants examined include Polysorbate 80 (e.g., Tween 80), Polysorbate 20 (e.g. Tween 20), NP-40, Triton X100, Triton X114, as well as polyoxyethylene alkyl ethers (e.g., Brij 35, and Brij 58). The HPV 16 samples at 20 mcg/mL protein were incubated with 0.01% of various surfactants respectively at room (ambient) temperature for 50 days. The incubation buffer contained 50 mM MOPS, 0.15 M NaCl at pH 7. All of the surfactants protect HPV 16 against aggregation during storage compared to a no surfactant control HPV 16 sample as determined by DLS (FIG. 11). The degree of protection at this surfactant concentration (0.01%) varies somewhat from surfactant to surfactant. To test the salt dependence of the protective ability of nonionic surfactants, HPV 16 samples at 30–60 mcg/mL protein were incubated for 24 hours at 4° C. with 0.01–0.02% Tween 80 and a NaCl concentration of 0.15–0.5 M. It was seen that NaCl concentrations of 0.2M or higher provide significant protection against HPV16 VLP aggregation in combination with nonionic surfactants.

The stabilizing effect of salt concentration against HPV aggregation in the presence of nonioinic surfactants was examined in terms of total ionic strength. FIG. 2 and FIG. 9 show that a minimum NaCl concentration is required to stabilize HPV VLP in the presence or absence of nonionic surfactants. In the following experiment, different salts were examined for their ability to stabilize HPV 16 VLP at a constant ionic strength. 60 mcg/ml HPV16 was incubated at 22° C. for 24 hours, then stored 4° C. until assayed for hydrodynamic size (Dh) by dynamic light scattering and by in vitro antigenicity (antibody binding) by EIA and BIA core analysis. Table 1 shows that when a variety of salts were used instead of NaCl, similar HPV stability was seen at lower salt concentrations but at the same ionic strength. As a control, a lower ionic strength solution resulted in HPV aggregation and partial loss of antigenicity. These results suggest that the salt stabilizing effect is predominated by ionic strength instead of salt type under these conditions. When a similar salt stabilizing effects were tested under more stressed conditions (37° C.), some variations of stabilizing ability between different salts were observed as shown by in vitro antigenicity assay and aggregation analysis. For example, $CaCl_2$ and $MgCl_2$ as well as phosphate buffer were less effective in stabilizing HPV VLPs at a constant ionic strength.

TABLE 1

|  | MOPS (M) | Added Salt (M) | Final Tween 80 | Total ionic strength (M) | Biacore*/ Protein | EIA*/ Protein | Dh (nm) |
| --- | --- | --- | --- | --- | --- | --- | --- |
| NaCl | 0.05 | 0.02 | 0.01% | 0.12 | 0.4 | 0.2 | 180 |
| NaCl | 0.05 | 0.12 | 0.01% | 0.22 | 1.0 | 1.0 | 72 |
| NaCitrate | 0.05 | 0.02 | 0.01% | 0.22 | 1.2 | 0.9 | 74 |
| Na Phosphate | 0.05 | 0.02 | 0.01% | 0.22 | 0.8 | 1.2 | 74 |
| NaAcetate | 0.05 | 0.12 | 0.01% | 0.22 | 1.0 | 1.0 | 74 |
| $Na_2SO_4$ | 0.05 | 0.04 | 0.01% | 0.22 | 0.8 | 1.1 | 73 |

TABLE 1-continued

|  | MOPS (M) | Added Salt (M) | Final Tween 80 | Total ionic strength (M) | Biacore*/ Protein | EIA*/ Protein | Dh (nm) |
|---|---|---|---|---|---|---|---|
| MgCl$_2$ | 0.05 | 0.04 | 0.01% | 0.22 | 1.0 | 1.1 | 74 |
| CaCl$_2$ | 0.05 | 0.04 | 0.01% | 0.22 | 0.8 | 1.2 | 93 |

*Relative in vitro antibody binding response was normalized to a −70° C. frozen control HPV 16 sample. The control was thawed immediately before the assay. Hydrodynamic diameter (Dh) of control sample by dynamic light scattering was measured as 73 nm.

Therefore, the presence of Polysorbate 80 at a concentration of as low as 0.01%, protects HPV 11 and HPV 16 from adsorption to container surfaces and from inter-particle aggregation at near physiologic ionic strength for weeks at 4° C. These data also show that (1) adsorption of HPV on surfaces and aggregation are related and (2) both electrostatic and hydrophobic mechanisms might be involved because neither detergents by themselves or a salt by itself can offer full protection against either adsorption or aggregation.

What is claimed is:

1. A non-alum human papilloma virus antigen formulation, which comprises:
   (a) a vaccine component comprising human papillomavirus virus-like particles;
   (b) a salt present at a physiologically acceptable concentration, wherein the salt is selected from the group consisting of sodium chloride, sodium sulfate, ammonium sulfate, sodium acetate, sodium citrate and sodium phosphate; and
   (c) a non-ionic surfactant present at a physiologically acceptable concentration, wherein the non-ionic surfactant is selected from the group consisting of polysorbates, polyoxyethylene alkyl ethers, Triton X-100®, Triton 114®, NP40®, Span 85 and the Pluronic series of non-ionic surfactants;
   wherein said antigen formulation is not combined with an alum-containing adjuvant.

2. The antigen formulation of claim 1 wherein said human papillomavirus vaccine component comprises virus-like particles.

3. The antigen formulation of claim 2 wherein said human papillomavirus virus like particles comprise either a L1 protein or an L1 and L2 protein.

4. The antigen formulation of claim 3 wherein said human papillomavirus virus like particles are selected from group of human papillomavirus types consisting of 6a, 6b, 11, 16, 18, and any combination thereof.

5. The antigen formulation of claim 4 wherein said salt is sodium chloride.

6. The antigen formulation of claim 5 wherein sodium chloride is present at a concentration from about 50 mM to about 500 mM.

7. The antigen formulation of claim 5 wherein sodium chloride is present at a concentration from about 150 mM to about 300 mM.

8. The antigen formulation of claim 7 wherein said polysorbate is Polysorbate 80.

9. The antigen formulation of claim 8 wherein Polysorbate 80 is present at a concentration to about 0.2% w/v.

10. The antigen formulation of claim 8 wherein said Polysorbate 80 is present at a concentration to about 0.01% w/v.

11. A non-alum human papilloma virus antigen formulation, which comprises:
  (a) a population of human papillomavirus virus-like particles comprised of the human papillomavirus L1 protein selected from the group consisting of 6a, 6b, 11, 16, and 18;
  (b) sodium chloride at a concentration from about 150 mM to about 300 mM; and,
  (c) Polysorbate 80 at a concentration up to about 0.1% w/v.

12. A method of stabilizing a population of purified virus-like particles derived from L1 or L1 and L2 protein of human papillomavirus at a temperatures above about 0° C. for a time period of at least one month to wbich comprises placing said purified virus-like particles in a non-alum formulation containing sodium chloride at a concentration from about 50 mM to about 500 mM and Polysorbate 80 at a concentration of up to at least 0.2% w/v.

13. The method of claim 12 wherein the vaccine formulation comprises sodium chloride in a concentration range from about 150 mM to about 300 mM.

14. The method of claim 13 wherein Polysorbate 80 is present at a concentration of up to at least 0.1% w/v.

15. The method of claim 12 wherein said formulation is stable at a temperature of about 2° C. to about 8° C. for a period of at least one month.

* * * * *